(12) United States Patent
Farrell et al.

(10) Patent No.: US 7,615,527 B2
(45) Date of Patent: Nov. 10, 2009

(54) PEPTIDES WHICH MODULATE BLOOD COAGULATION AND METHODS OF USE THEREOF

(75) Inventors: David H. Farrell, Tualatin, OR (US); Rehana S. Lovely, Tigard, OR (US)

(73) Assignee: Oregon Health & Science University, Portland, OR (US)

( * ) Notice: Subject to any disclaimer, the term of this patent is extended or adjusted under 35 U.S.C. 154(b) by 700 days.

(21) Appl. No.: 10/482,175

(22) PCT Filed: Jul. 8, 2002

(86) PCT No.: PCT/US02/21543

§ 371 (c)(1),
(2), (4) Date: Jul. 7, 2004

(87) PCT Pub. No.: WO03/003988

PCT Pub. Date: Jan. 16, 2003

(65) Prior Publication Data

US 2004/0248807 A1    Dec. 9, 2004

Related U.S. Application Data

(60) Provisional application No. 60/303,658, filed on Jul. 6, 2001, provisional application No. 60/315,093, filed on Aug. 27, 2001.

(51) Int. Cl.
*A61K 38/00*    (2006.01)
*C07K 11/00*    (2006.01)
(52) U.S. Cl. .......................................... 514/2; 530/300
(58) Field of Classification Search ........................ None
See application file for complete search history.

(56) References Cited

U.S. PATENT DOCUMENTS

| 4,346,078 | A | | 8/1982 | Bajusz et al. |
| 5,457,090 | A | | 10/1995 | Scott et al. |
| 5,705,606 | A | * | 1/1998 | Charo et al. ............... 530/300 |
| 5,858,350 | A | | 1/1999 | Vournakis et al. |
| 2002/0119572 | A1 | * | 8/2002 | Jacobson et al. ............ 435/466 |

FOREIGN PATENT DOCUMENTS

WO    WO 98/12318    3/1998

OTHER PUBLICATIONS

Rixon et al. Biochemistry 24: 2077-2086 (1985).*
Farrell et al., "Recombinant Human Fibrinogen and Sulfation of the Gamma' Chain", Biochemistry 30: 9414-9420 (1991).*
Collet, J.P., et al., "Influence of γ' Fibrinogen Splice Variant on Fibrin Physical Properties and Fibrinolysis Rate", Arterioscler. Throm. Vasc. Biol., vol. 24: p. 1-6 (2004).
Farrell, D.H., "Pathophysiologic roles of fibrinogen gamma chain", Current Opinion in Hematology, vol. 11: pp. 151-155.
Lovely, R.S., et al., "Fibrinogen γ' chain binds thrombin exosite II", J. of Thrombosis and Haemostasis, vol. 1: 124-131, (2002).
Pospisil, C.H., et al., "Evidence That Both Exosites on Thrombin Participate in Its High Affinity Interaction with Fibrin", J. of Biol. Chem., vol. 278: pp. 21584-21591 (2003).
Cooper, A.V., et al., "Fibrinogen gamma-chain splice varient γ' alters fibrin formation and structure", Blood, vol. 102, pp. 535-540, (2003).
Podor, T.J., et al., "Incorporation of Vitronectin into Fibrin Clots", J. of Biol. Chem., vol. 277: pp. 7520-7528, (2002).
Lovely, R.S., et al., "Association of γA/γ' Fibrinogen Levels and Coronary Artery Disease", Thromb. Haemost., vol. 88: pp. 26-31, (2002).
De Bosch, N.B., et al., "Inhibition of Thrombin Generation in Plasma by Fibrin Formation (Antithrombin I)", Thromb. Haemost., vol. 88: 253-8, (2002).
Meh, D.A., et al., "The Amino Acid Sequence in Fibrin Responsible for High Affinity Thrombin Binding", Thromb. Haemost., vol. 85: 470-4, (2001).
Dallabrida, S.M., et al., "Factor XIIIa supports microvascular endothelial cell adhesion and inhibits capillary tube formation in fibrin", Blood, vol. 95: pp. 2586-2592, (2000).
Moaddel, M., et al., "The Role of γA/γ' Fibrinogen in Plasma Factor XIII Activation", J. of Biological Chemistry, vol. 275: pp. 32135-32140, (2000).
Moaddel, M., et al., "Interactions of Human Fibrinogens with Factor XIII: Roles of Calcium and the γ' Peptide", Biochemistry, vol. 39: pp. 6698-6705, (2000).
Falls, L.A., et al., "Resistance of γA/γ' Fibrin Clots to Fibrinolysis", J. of Biological Chemistry, vol. 272: pp. 14251-14256, (1997).
Siebenlist, K.R., et al., "Plasma Factor XIII Binds Specifically to Fibrinogen Molecules Containing γ' Chains", Biochemistry, vol. 35: pp. 10448-10453, (1996).
Meh, D.A., et al., "Identification and Characterization of the Thrombin Binding Sites on Fibrin", J. of Biological Chemistry, vol. 271: pp. 32121-32125, (1996).
Hofsteenge, J. "The effect of substituting phosphotyrosine for sulphtyrosine on the activity of hirudin"; Eur. J. Biochem., 188: 55-59(1990).
Hortin, G.L., et al., "Inhibition of thrombin's clotting activity by synthetic peptide segments of its inhibitors and substrates," Biochem. Biophys. Res. Comm., 169(2):437-442, (Jun. 15, 1990).
Farrell, D.H., "Pathophysiologic roles of fibrinogen gamma chain", Current Opinion in Hematology, vol. 11: pp. 151-155, 2004.

* cited by examiner

*Primary Examiner*—Anand U Desai
(74) *Attorney, Agent, or Firm*—Dann, Dorfman, Herrell & Skillman; Robert C. Netter, Jr.; Kathleen D. Rigaut

(57) ABSTRACT

Peptide fragments that modulate thrombosis and methods of use thereof are provided. Also provided are synthetic bioactive anti-coagulation peptides, compositions comprising such peptides and methods for the administration to patients in need thereof.

33 Claims, 15 Drawing Sheets

| Chain | Carboxyl Sequence |
|---|---|
| γA | AGDV |
| γ' | VRPEHPAETEYDSLYPEDDL |
| γ' Y418F | VRPEHPAETEE̲DSLYPEDDL |
| γ' Y422F | VRPEHPAETEYDSLF̲PEDDL |
| γ' Y418F/Y422F | VRPEHPAETEE̲DSLF̲PEDDI |

Figure 1

193 kDa- 112 kDa- 86 kDa-
70 kDa- 57 kDa-

-γ' chain 40 kDa-
36 kDa- 1 2 3 4 5 6

PEPTIDES WHICH MODULATE BLOOD COAGULATION AND METHODS OF USE THEREOF

This application is a §371 application of PCT/US02/21543 filed 8 Jul. 2002, which in turn claims priority to U.S. Provisional Application Ser. No. 60/303,658, filed Jul. 6, 2001 and U.S. Provisional Application Ser. No. 60/315,093, filed Aug. 27, 2001. The entire disclosure of each of the above identified applications is incorporated by reference herein.

Pursuant to 35 U.S.C. §202(c) it is acknowledged that the U.S. Government has certain rights in the invention described herein, which was made in part with funds from the National Institutes of Health, Grant Numbers, R29HL53997 and KO2HL04215.

FIELD OF THE INVENTION

This invention relates to novel compositions and methods of use thereof for modulating thrombosis. More specifically, novel peptide fragments that act as anti-coagulants are provided. These novel peptide fragments may be used to advantage as therapeutic agents for the inhibition of blood coagulation to prevent thrombosis.

BACKGROUND OF THE INVENTION

Several publications and patent documents are referenced in this application by author name, year and journal of publication or number in parentheses in order to more fully describe the state of the art to which this invention pertains. The disclosure of each of these publications is incorporated by reference herein.

Thrombin is the final protease in the blood coagulation cascade, and converts soluble fibrinogen to an insoluble fibrin clot. Fibrin/fibrinogen interacts with thrombin in several distinct ways. First, fibrinogen serves as a substrate for thrombin, in which thrombin cleaves short fibrinopeptides of 16 and 14 amino acids, respectively, from the amino termini of the α and β chains of fibrinogen (1). In addition, thrombin can also bind to fibrin at sites that are distinct from thrombin's catalytic site (2). Fibrin contains both high and low affinity sites for thrombin (3). A low affinity site has been mapped to the central E domain of fibrin (4), and involves residues α23-51 (5) and the newly-exposed amino terminus residues β15-42 (3). These low affinity interactions are believed to facilitate thrombin cleavage of the fibrinopeptides. In addition to the low affinity thrombin binding sites, fibrin also contains high affinity binding sites. Studies by Meh et al. (3, 6) showed that a high affinity thrombin binding site is located on the γ' chain of fibrinogen.

The γ' (or γB) chain arises from alternative processing of the γ chain mRNA (7, 8), and constitutes about 7% of the total γ chains in fibrinogen (9). The γ' chain carboxyl terminus is highly anionic, with seven Glu/Asp residues within the last seventeen amino acids, and contains tyrosine O-sulfate residues (6, 10). γ'-chain containing fibrinogen consists primarily of a heterodimer with one γ' chain and one γA chain, while the more common form of fibrinogen contains two γA chains (11, 12). Earlier studies on thrombin binding to fibrin fragments (4) showed no binding to the D domain of fibrinogen where the γ' chain resides. However, the carboxyl terminus of the γ' chain is cleaved by plasmin during fibrinolysis (13), which may explain the lack of thrombin binding seen in these earlier studies with fragment D.

Binding of thrombin to these sites has important physiologic consequences. Clot-bound thrombin is resistant to inactivation by its natural plasma inhibitor, ATIII, even in the presence of the anticoagulant glycosaminoglycan, heparin (14, 15). In the absence of heparin, heparin increases the rate of thrombin inactivation by ATIII by forming a ternary-complex with thrombin and ATIII (16). Fibrin also increases thrombin's amidolytic and proteolytic activities (17). In addition, in vitro data shows that clots made from γA/γ' fibrinogen are resistant to fibrinolysis by plasmin. This may be due, at least in part, to increased crosslinking by factor XIIIa (18), a plasma transglutaminase that is activated by thrombin. Factor XIII is activated more rapidly in the presence of γA/γ fibrin than γA/γA fibrin (17).

The binding site on thrombin for the γ' chain has been the focus of intense research. Two potential binding sites for the highly negatively-charged γ' chain include anion-binding exosites I and II (19). Exosite I binds to fibrinogen near the amino terminus to facilitate fibrinopeptide cleavage (20), and can bind to heparin cofactor II (21) or to the thrombin receptor (22) as well. The leech salivary anticoagulant protein, hirudin, also binds to exosite I and prevents fibrinogen binding (23). In contrast to exosite I, exosite II is often considered to be a glycosaminoglycan binding site that mediates heparin-accelerated inhibition by ATIII (24, 25), and binds chondroitin sulfate residues in thrombomodulin (26). However, exosite II also binds a proteinaceous ligand, the platelet cell-surface thrombin receptor, GPIbα (27).

The above-mentioned studies demonstrate that thrombin, fibrinogen and fragments thereof are involved in a myriad of pathways critical for maintaining the quality and duration of the blood clotting reaction. Reagents which specifically modulate the activity of these proteins are desirable for the treatment of pathological disorders associated with aberrant clotting activity, such as thrombosis.

SUMMARY OF THE INVENTION

In accordance with the present invention, there is provided a peptide having anticoagulant and anti-platelet activity, comprising the amino acid sequence PEHPAETEYDSLYPEDDL (SEQ ID NO: 1), wherein the amino acid residues at positions 9 and 13 are modified to increase the anionic character of the peptide. In a preferred embodiment of the invention amino acid residues 9 and 13 are phosphorylated.

Compositions comprising the modified peptide in a pharmaceutically acceptable carrier constitute another aspect of the invention.

In yet a further aspect of the invention, methods for inhibiting thrombosis in a patient in need thereof are provided. The method entails the administration of the phosphorylated peptide of the invention in an amount effective to prevent or reduce thrombotic events.

In another aspect of the invention, methods for making synthetic anti-coagulation peptide precursors using recombinant DNA technology are provided. Exemplary peptide precursors have the following generic structure:

signal sequence-tag sequence-spacer sequence--2, −1 cleavage site-γ' 18-mer.

Representative synthetic anti-coagulation peptide precursors have the following sequences:

i) MSWSLHPRNLILYFYALLFLSSTCVAHHHHHHAA AAAAAAAAAAAAAAVRPEHPAETEYDSLYPEDDL (SEQ ID NO: 2);

ii) MFSMRIVCLVLSVVGTAWTMDYKDDDDKPEHPA ETEYDSLYPEDDL (SEQ ID NO: 3); a spacer sequence of polyalanine (10-20 residues) may optionally be inserted between K and P; and iii) MKHLLLLLLLCVFLVKSEQKLISEEDLEXXYXQSP EHPAETEYDSLYPEDDL (SEQ ID NO: 4); a spacer sequence of polyalanine (10-20 residues) may optionally be inserted between S and P. Each of the tyrosine residues present in peptides i), ii), and iii) are optionally modified by a sulfate or a phosphate group.

In another aspect of the invention, synthetic anti-coagulation peptides selected from the group consisting of SEQ ID NOs: 17-47, wherein tyrosine residues are modified to increase the anti-coagulation activity of the peptide, are provided. In a preferred embodiment, tyrosine residues of these synthetic anti-coagulation peptides contain a modification selected from the group consisting of sulfation and phosphorylation.

In another aspect of the invention, synthetic anti-coagulation peptides comprising at least one amino acid substitution selected from the group of a valine substituted for a threonine and a valine substituted for a serine are provided. Also provided herein are synthetic anti-coagulation peptides comprising conservative amino acid substitutions.

Compositions containing the aforementioned anti-coagulation peptides in a pharmaceutically acceptable carrier are also included in the scope of the present invention, as are methods of administration of the synthetic anti-coagulation peptides to patients in need thereof.

Also provided are assays to screen for modulators of anti-coagulation peptide activity.

BRIEF DESCRIPTION OF THE DRAWINGS

FIG. 1 shows sequences of γA (SEQ ID NO: 52), γ' (SEQ ID NO: 11), and recombinant mutant γ' chain carboxyl termini (γ: Y418F-SEQ ID NO: 53; γ' Y422F-SEQ ID NO: 54; γ' Y418F/Y422F-SEQ ID NO: 55).

DETAILED DESCRIPTION OF THE INVENTION

Figure 2:
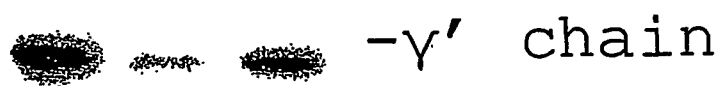
FIG. 2 shows immunoprecipitation of $^{35}SO_4$-labeled recombinant fibrinogens.

In accordance with the present invention, a synthetic peptide that corresponds in amino acid sequence to the carboxyl terminal 18 amino acids in the γ' chain of fibrinogen, PEHPAETEYDSLYPEDDL (SEQ ID NO: 1), but contains phosphotyrosine residues in place of the natural sulfotyrosine residues at amino acids 9 and 13 (equivalent to amino acids 418 and 422 in the native γ' chain) is provided. The γ' peptide acts an anticoagulant and anti-platelet agent. The γ' peptide of the invention provides a non-immunogenic anticoagulant that acts as an anticoagulant in blood, without causing heparin-induced thrombocytopenia, a potentially fatal complication of heparin administration that occurs in 1-3% of heparin transfusions lasting a week or more. Finally, the γ' peptide described herein displaces fibrin clot-bound thrombin, which is naturally resistant to heparin, as it binds to fibrin through its heparin-binding site.

Fibrin/fibrinogen contains distinct high and low affinity binding sites for thrombin. In accordance with the present invention, a high affinity thrombin binding site in an alternatively-processed fibrinogen γ chain variant, the γ' chain, has been discovered. The binding site is contained within the carboxyl terminal twenty amino acids of the γ' chain, and Tyr 418 and 422 in this part of the γ' chain are shown to be sulfated. A peptide corresponding to the carboxyl terminal twenty amino acids of the γ' chain, γ' 408-427, binds thrombin with a $K_d=0.43\pm0.08$ μM. Competitive binding studies with hirudin peptides, heparin, DNA aptamers, and a monoclonal antibody directed against thrombin exosite II showed that thrombin-binds to the γ' peptide through exosite II. Several of these exosite ligands contain tyrosine O-sulfate residues, and in some cases tyrosine sulfation has been shown to increase the binding affinity. For example, non-tyrosine sulfated hirudin binds with ~10-fold lower affinity to thrombin than the sulfated form (28). In addition, heparin cofactor II (30) and GPIbα (31) also contain tyrosine O-sulfate residues that are required for maximal thrombin binding. Two thrombin substrates, factor V (32) and factor VIII (33), contain tyrosine O-sulfate residues that are required for optimal cleavage rates by thrombin. Therefore, tyrosine O-sulfation plays a role in thrombin binding to several different ligands. In peptide mimetics based on the human fibrinogen γ' chain, sulfation at positions γ'Y418 and γ'Y422 results in higher affinity binding to thrombin (6). In addition, the predicted molecular weight of the γ' chain as measured by mass spectrometry is 151 Da larger than predicted by primary sequence analysis (assuming monosialyation at the γ' chain glycosylation site), suggestive of tyrosine sulfation at two residues (6). However, while these results are consistent with tyrosine sulfation on both γ' 418 and γ' 422, the actual sulfated residues had not been identified directly prior to the results presented herein (48).

The results presented herein indicate that γ-thrombin binds the γ' 408-427 peptide with a similar affinity to that of α-thrombin. Thus, thrombin appears to bind to the γ' chain through exosite II, leaving exosite I and the active site accessible to substrates. Following plasmin cleavage, this thrombin binding site is removed from γA/γ fibrin. This may explain why fibrin-bound thrombin is resistant to heparin and can retain enzymatic activity.

I. DEFINITIONS

The following definitions are provided to facilitate an understanding of the present invention.

With reference to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule. An isolated nucleic acid molecule inserted into a vector is also sometimes referred to herein as a "recombinant" nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., 1989):

$$T_m = 81.5° C. + 16.6 \text{ Log } [Na+] + 0.41(\% G+C) - 0.63(\% \text{ formamide}) - 600/\#bp \text{ in duplex}$$

As an illustration of the above formula, using [Na+]= [0.368] and 50% formamide, with GC content of 42% and an 3 average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

Amino acid residues described herein are preferred to be in the "L" isomeric form. However, residues in the "D" isomeric form may be substituted for any L-amino acid residue, provided the desired properties of the polypeptide are retained. All amino-acid residue sequences represented herein conform to the conventional left-to-right amino-terminus to carboxy-terminus orientation.

Amino acid residues are identified in the present application according to the three-letter or one-letter abbreviations in the following Table:

TABLE 1

| Amino Acid | 3-letter Abbreviation | 1-letter Abbreviation |
| --- | --- | --- |
| L-Alanine | Ala | A |
| L-Arginine | Arg | R |
| L-Asparagine | Asn | N |
| L-Aspartic Acid | Asp | D |
| L-Cysteine | Cys | C |
| L-Glutamine | Gln | Q |
| L-Glutamic Acid | Glu | E |
| Glycine | Gly | G |
| L-Histidine | His | H |
| L-Isoleucine | Ile | I |
| L-Leucine | Leu | L |
| L-Methionine | Met | M |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |
| L-Lysine | Lys | K |

The term "conservative amino acid substitution" as used herein refers to an alteration in an amino acid position of a polypeptide, wherein the alteration is not predicted to alter the function and/or structure of the altered polypeptide. Such substitutions are based on Blossom 62 Matrix analyses and are known to those of skill in the art. Table 2 provides a list of amino acid substitutions which are generally considered to be conservative in nature.

TABLE 2

| Group | Amino Acid | Properties |
| --- | --- | --- |
| I | A, V, L, I, M, G | Aliphatic |
| II | S, T, C | Hydroxyl/Sulfhydryl/Polar |
| III | N, Q | Amide Side Chains |
| IV | F, W, Y | Aromatic |
| V | H, K, R | Basic |
| VI | D, E | Acidic |

Conservative amino acid substitutions may include the substitution of one amino acid residue for another amino acid residue categorized in the same group (as listed above in Table 2). Exemplary Group I amino acids which may be substituted include: A, V, L, and I. Exemplary Group II amino acids which may be substituted for each other include: S and T. Of the Group V amino acids, K and R may be used interchangeably. Exemplary Group VI residues which may be substituted interchangeably include: K and R.

Alternatively, a BLOSUM62 Substitution Matrix may be used to predict or determine the effect of an amino acid substitution in the context of a particular polypeptide. Details regarding the BLOSUM62 Substitution Matrix are provided on the worldwide web at blc.arizona.edu/courses/bioinformatics/blosum.html, the entire contents of which is incorporated herein by reference.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

"Mature protein" or "mature polypeptide" shall mean a polypeptide possessing the sequence of the polypeptide after any processing events that normally occur to the polypeptide during the course of its genesis, such as proteolytic processing from a polyprotein precursor. In designating the sequence or boundaries of a mature protein, the first amino acid of the mature protein sequence is designated as amino acid residue 1. As used herein, any amino acid residues associated with a mature protein not naturally found associated with that protein that precedes amino acid 1 are designated amino acid -1, -2, -3 and so on. For recombinant expression systems, a methionine initiator codon is often utilized for purposes of efficient translation. This methionine residue in the resulting polypeptide, as used herein, would be positioned at −1 relative to the mature protein sequence.

A low molecular weight "peptide analog" shall mean a natural or mutant (mutated) analog of a protein, comprising a linear or discontinuous series of fragments of that protein and which may have one or more amino acids replaced with other amino acids and which has altered, enhanced or diminished biological activity when compared with the parent or nonmutated protein.

The term "biological activity" is a function or set of functions performed by a molecule in a biological context (i.e., in an organism or an in vitro surrogate or facsimile model).

The term "substantially pure" refers to a preparation comprising at least 50-60% by weight the compound of interest (e.g., nucleic acid, oligonucleotide, polypeptide, protein, etc.). More preferably, the preparation comprises at least 75% by weight, and most preferably 90-99% by weight, the compound of interest. Purity is measured by methods appropriate for the compound of interest (e.g. chromatographic methods, agarose or polyacrylamide gel electrophoresis, HPLC analysis, mass spectrometry and the like).

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, of that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by the trained artisan, and are contemplated to be within the scope of this definition.

A "vector" is a replicon, such as a plasmid, cosmid, bacmid, phage or virus, to which another genetic sequence or element (either DNA or RNA) may be attached so as to bring about the replication of the attached sequence or element. The attached sequence can encode at least one heterologous protein of interest, e.g., a peptide of the invention. Other signals which facilitate expression in the desired host cell, e.g., 5' and 3' regulatory sequences may also be incorporated into the vector.

A "signal sequence" is a conserved stretch of amino acids which direct secretion or intracellular transport of proteins containing such sequences. Signal sequences may direct nuclear, cytoplasmic or organellar localization of proteins. They may also direct extracellular secretion of proteins.

A "sulfation signal" is a conserved sequence motif that is recognized by tyrosylprotein sulfotransferase which transfers a sulfate residue to tyrosine residues within the sequence motif.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the basic and novel characteristics of the sequence.

An "immune response" signifies any reaction produced by an antigen, such as a viral antigen, in a host having a functioning immune system. Immune responses may be either humoral in nature, that is, involve production of immunoglobulins or antibodies, or cellular in nature, involving various types of B and T lymphocytes, dendritic cells, macrophages, antigen presenting cells and the like, or both. Immune responses may also involve the production or elaboration of various effector molecules such as cytokines, lymphokines and the like. Immune responses may be measured both in vitro and in various cellular or animal systems. Such immune responses may be important in protecting the host from disease and may be used prophylactically and therapeutically.

An "antibody" or "antibody molecule" is any immunoglobulin, including antibodies and fragments thereof, that binds to a specific antigen. The term includes polyclonal, monoclonal, chimeric, and bispecific antibodies. As used herein, antibody or antibody molecule contemplates both an intact immunoglobulin molecule and an immunologically active portion of an immunoglobulin molecule such as those portions known in the art as Fab, Fab', F(ab')2 and F(v).

With respect to antibodies, the term "immunologically specific" refers to antibodies that bind to one or more epitopes of a protein or compound of interest, but which do not substantially recognize and bind other molecules in a sample containing a mixed population of antigenic biological molecules.

As used herein, phosphorylation refers to the covalent coupling of a phosphate group to the hydroxyl group of a tyrosine, serine, or threonine molecule. Phosphorylation may occur from either chemical or enzymatic means. Enzymes that phosphorylate tyrosine, serine, or threonine molecules are referred to as kinases.

As used herein, sulfation refers to the covalent coupling of a sulfate group to the hydroxyl group of a tyrosine, serine, or threonine amino acid. Sulfation may occur from either chemical or enzymatic means. However, of tyrosine, serine, and threonine amino acids, only sulfation of tyrosine molecules occurs naturally through enzymatic means. Enzymes that sulfate tyrosine molecules are referred to as tyrosylprotein sulfotransferases.

As used herein, "anticoagulant activity" or "anti-coagulation activity" refers to an activity which abrogates or inhibits either or both primary and secondary haemostasis.

As used herein, the term γ' peptide or a derivative thereof refers to a polypeptide selected from the group of polypeptides consisting of SEQ ID NOs: 17-47, each of which may further comprise at least one tyrosine modified by phosphorylation and at least one tyrosine modified by sulfation. Such γ' peptides or derivatives thereof may optionally further comprise at least one amino acid substitution selected from the group consisting of a valine substituted for a threonine, a valine substituted for a serine, and conservative amino acid substitutions as described herein. γ' peptides or derivatives thereof may optionally be acylated, for example, by acetylation at the amino terminus.

As used herein, an in vitro assay system refers' to an assay which is performed in vitro and may be used to detect biological activity. Exemplary in vitro assay systems useful for detecting anti-coagulation activity include: activated partial thromboplastin time assays, platelet aggregometry assays, prothrombin time assays, platelet function analyzer assays, and fibrinopeptide cleavage assays.

As used herein, an in vivo assay system refers to an assay which is performed in vivo and may be used to detect biological activity. Exemplary in vivo assay systems useful for detecting anti-coagulation activity include: modified ferric chloride injury models and shunt thromobosis models.

II. PREPARATION OF NUCLEIC ACID MOLECULES

Nucleic acid molecules encoding the peptides of the invention may be prepared by two general methods: (1) synthesis from appropriate nucleotide triphosphates, or (2) isolation from biological sources. Both methods utilize protocols well known in the art. The availability of nucleotide sequence information, such as the DNA sequences encoding γ' peptide of the invention, enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be used directly or purified according to methods known in the art, such as high performance liquid chromatography (HPLC).

III. PREPARATION OF PEPTIDE ANALOGS

A peptide analog of the present invention can be made by exclusively solid phase techniques, by partial solid-phase techniques, by fragment condensation, by classical solution coupling, or, as long as the analog consists of only amino acids among the twenty naturally occurring amino acids corresponding to codons of the genetic code, by employing recombinant DNA techniques. Suitable host organisms for this purpose include, without limitation, *E. coli, B. subtilis, S. cerevisiae, S. pombe* and *P. pastoris*. Alternatively, insect or mammalian cells may be utilized.

Methods of making a polypeptide of known sequence by recombinant DNA techniques are described herein and are well-known in the art. See, e.g., U.S. Pat. No. 4,689,318, which is incorporated herein by reference.

Methods for chemical synthesis of polypeptides are also well-known in the art and, in this regard, reference is made, by way of illustration, to the following literature: Yamashino and Li, *J Am Chem Soc* 100:5174-5178, 1978; Stewart and Young, Solid Phase Peptide Synthesis (WH Freeman and Co. 1969); Brown et al., *JCS Peritin I,* 1983, 1161-1167; M. Bodanszky et al., *Bioorg Chem* 2:354-362, 1973; U.S. Pat. Nos. 4,689,318; 4,632,211; 4,237,046; 4,105,603; 3,842,067; and 3,862,925, all of which are incorporated herein by reference.

The chemical modifications in the 18 amino acid γ' peptide include phosphorylation of tyrosine amino acids at positions 9 and 13, corresponding to amino acids 418 and 422 in the native protein. These two modifications are required for maximum binding affinity to thrombin. Without these modifications, binding of the unmodified peptide to thrombin is too weak for biological activity. Phosphorylation of the tyrosine amino acids can be accomplished by direct incorporation of phosphorylated tyrosine amino acids into the peptide during chemical peptide synthesis, or by chemical or enzymatic methods following chemical peptide synthesis or peptide synthesis using recombinant DNA techniques. Expression of the γ' peptide in appropriate host cells may also be used to mediate the phosphorylation of the peptide by endogenous or exogenously expressed kinases in such host cells.

Chemical modifications to the 18 amino acid γ' peptide also include sulfation of tyrosine amino acids at positions 9 and 13, corresponding to amino acids 418 and 422 in the native protein. As described above, such modifications are required for maximum binding affinity to thrombin. Sulfation of the tyrosine amino acids can be accomplished by direct incorporation of protected sulfo-tyrosines into the peptide during chemical peptide synthesis, or by chemical or enzymatic methods following chemical peptide synthesis or peptide synthesis using recombinant DNA techniques. Expression of the γ' peptide in appropriate host cells may also be used to mediate the sulfation of the peptide by endogenous or exogenously expressed sulfotransferases in such host cells. Recombinant γ' fibrinogen, for example, is sulfated when expressed in mammalian cells (10). Recombinant vitronectin has also been shown to be sulfated on tyrosine residues when expressed in SF9 cells (47). Methods for the expression of such sulfated recombinant polypeptides, as set forth in the above-mentioned references, are incorporated herein by reference.

IV. ADMINISTRATION OF PEPTIDE ANALOGS

The peptide analogs as described herein will generally be administered to a patient as a pharmaceutical preparation. The term "patient" as used herein refers to human or animal subjects. These protein analogs may be employed therapeutically, under the guidance of a health care professional for the inhibition of blood coagulation to prevent thrombosis. Administration is preferably in a "prophylactically effective amount" or a "therapeutically effective amount" (as the case may be, although prophylaxis may be considered therapy), this being sufficient to show benefit to the individual.

The dose and dosage regimen of an analog according to the invention that is suitable for administration to a particular patient may be determined by a physician considering the patient's age, sex, weight, general medical condition, and the specific condition and severity thereof for which the peptide analog is being administered. The health care professional may also consider the route of administration of the peptide analog, the pharmaceutical carrier with which the peptide analog may be combined, and the peptide analog's biological activity.

Selection of a suitable pharmaceutical preparation depends upon the method of administration chosen. For example, peptide analogs may be administered parenterally by intravenous injection into the blood stream, or by subcutaneous, intramuscular or intraperitoneal injection. Pharmaceutical preparations for parenteral injection are known in the art. If parenteral injection is selected as a method for administering the peptide analogs, steps must be taken to ensure that sufficient amounts of the molecules reach their target cells to exert a biological effect. For example, when brain tissues are targeted, the lipophilicity of the peptide analogs, or the pharmaceutical preparation in which they are delivered may have to be increased so that the molecules can cross the blood-brain barrier to arrive at their target locations. Furthermore, the peptide analogs may have to be delivered in a cell-targeting carrier so that sufficient numbers of molecules will reach the target site. Methods for increasing the lipophilicity of a molecule are known in the art.

Generally, intravenous injection to a final blood stream concentration of ~1 mM, by bolus injection, by infusion over a period of about 5 minutes to about 60 minutes, or by continuous infusion is sufficient for therapeutic efficacy. In vitro studies using reference blood plasma show that concentrations of 1 mM peptide prolong the blood clotting time from 29.0±0.1 seconds to 55.1±0.0 seconds in an activated partial thromboplastin assay, a common clinical assay used to assess blood clotting times. This prolongation of blood clotting time is a hallmark of effective anticoagulant therapy, such as occurs with heparin. Aerosol inhalation to a final blood stream concentration of ~1 mM may also be sufficient for efficacy.

The peptide analogs of the invention, or a pharmaceutically acceptable salt thereof, can be combined, over a wide concentration range (e.g., 0.001 to 11.0 wt %) with any standard pharmaceutical carrier (e.g., physiological saline, THAM solution, or the like) to facilitate administration by any of various routes including intravenous, subcutaneous, intramuscular, oral, or intranasal, including by inhalation.

Pharmaceutically acceptable salts of the peptide analogs of the invention can be prepared with any of a variety of inorganic or organic acids, such as for example, sulfuric, phosphoric, hydrochloric, hydrobromic, nitric, citric, succinic, acetic, benzoic and ascorbic. The peptide analogs can, for example, be advantageously converted to the acetate salt by dissolution in an aqueous acetic acid solution (e.g., 10% solution) followed by lyophilization.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the peptide or peptide analogs in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain dosage units, e.g., tablet, capsule, powder, injection, teaspoonful and the like, from about 0.001 to about 10 mg/kg, and preferably from about 0.01 to about 0.1 mg/kg of the active ingredient.

V. ASSAYS TO EVALUATE THE ANTI-COAGULATION PROPERTIES OF PEPTIDE ANALOGS AND IDENTIFY MODULATORS THEREOF

The present invention also provides assays to evaluate the anti-coagulation properties of fibrinogen γ' peptides. Such assays are described in Example III. Exemplary assays to detect and quantitate anti-coagulation activity of γ' peptides include: activated partial thromboplastin time (aPTT) assays and platelet aggregometry assays. The aPTT assay may be used to advantage as an anticoagulant assay for the γ' peptides due to its sensitivity to heparin-like compounds, its ease of use, and the ability to automate the procedure. The platelet aggregometry assay may be used to test the effects of a γ' peptide on platelet aggregation in platelet-rich plasma. In this assay, the activity of a γ' peptide may be determined in the presence or absence of epinephrine, ADP, collagen, ristocetin, arachidonic acid, and thrombin.

The assays described herein also provide means to screen for agents or test substances capable of modulating γ' peptide activity. Modulators of γ' peptide activity may be identified based on their ability to augment or abrogate the ability of a γ' peptide to effect coagulation in such assays. Modulators identified may be used to advantage in the treatment of patients in need thereof. In some clinical settings (e.g., wherein a patient is exhibiting symptoms of uncontrolled bleeding or the potential for hemorrhage), it may be advisable to administer an agent capable of inhibiting the anti-coagulation activity of a γ' peptide. Alternatively, the identification of an agent capable of increasing the anti-coagulation activity of a γ' peptide would provide a clinician with a useful reagent to use alone or in combination with a γ' peptide. Exemplary modulators of γ' peptide activity include: protamine-like polycationic peptides having anti-heparin activity and monoclonal antibodies specific for γ' peptides of the invention. Protamine-like polycationic peptides having anti-heparin activity are described in U.S. Pat. Nos. 5,721,212; 5,614,494; and 5,534,619, which are incorporated herein by reference in their entirety.

Monoclonal antibodies to fibrinogen γ' chain, which react with the γ' peptides of the invention have been described in Lovely et al. (49), the entire contents of which is incorporated herein by reference. Briefly, a monoclonal antibody immunologically specific for the γ' chain (2.G2.H9) was generated following immunization with a synthetic peptide corresponding to the carboxyl terminal twenty amino acids of the γ' chain, VRPEHPAETEYDSLYPEDDL, coupled to keyhole limpet hemocyanin as a carrier protein. 2.G2.H9 recognized γA/γ fibrinogen exclusively, and did not cross-react measurably with γA/γA fibrinogen.

The following examples are provided to illustrate various embodiments of the invention. They are not intended to limit the invention in any way.

EXAMPLE I

The Fibrinogen γ' Peptide has Potent Anti-Coagulation Activity

The following protocols are provided to facilitate the practice of Example I.

Proteins, Peptides, and DNA Aptamers. Human α-thrombin was generously provided by Dr. John Fenton, II (New York State Department of Health, Albany, N.Y.) and Dr. Walter Kisiel (University of New Mexico, Albuquerque, N. Mex.). Human γ-thrombin was obtained from Haematologic Technologies, Inc. (Essex Junction, Vt.). Tyrosine-phosphorylated derivatives of peptides corresponding to the γ' chain carboxyl terminus, VRPEHPAETEYDSLYPEDDL (SEQ ID NO: 11), were obtained from Research Genetics, Inc. (Huntsville, Ala.) and GeneMed Synthesis, Inc. (South San Francisco, Calif.). The peptides were purified to >95% purity by HPLC, and their molecular weights were verified by mass spectrometry. Tyrosine-sulfated, amino-terminal acetylated hirudin peptide 53-65 was obtained from Bachem, Inc. (Torrance, Calif.) and tyrosine-sulfated hirudin peptide 54-65 was obtained from Sigma (St. Louis, Mo.). Single-stranded DNA aptamers 5'-GGT-TGG-TGT-GGT-TGG-3' (SEQ ID NO: 5), referred to as HD1, and 5'-AGT-CCG-TGG-TAG-GGC-AGG-TTG-GGG-TGA-CT-3' (SEQ ID NO: 6), referred to as HD22, were generously provided by Dr. Jeffrey I. Weitz (McMaster University, Hamilton, ONT, Canada). A monoclonal antibody directed against thrombin exosite II (34) was a gift from Dr. Douglas M. Tollefsen (Washington University, St. Louis, Mo.).

Production of Recombinant Fibrinogens Recombinant fibrinogen molecules were expressed with tyrosine to phenylalanine mutations in the γ' chain at positions γ' 418 and/or γ' 422. Plasmid pAG-γ' (10) was used as the template for site-directed mutagenesis (35) using the primer GAA-ACA-GAA-T$\underline{TT}$-GAC-TCA-CTT (SEQ ID NO: 7) for Y418F, GAC-T$\underline{C}$A-CTT-T$\underline{T}$C-CCT-GAG-GAT (SEQ ID NO: 8) for Y422F, and GAA-ACA-GAA-T$\underline{TT}$-GAC-TCA-CTT-T$\underline{T}$C-CCT-GAG-GAT (SEQ ID NO: 9) for Y418F/Y422F. The mutated pAG-γ' plasmids were co-transfected with pBD-1 into a baby hamster kidney cell line as described previously (10). Recombinant fibrinogens were labeled with 1 mCi/ml $^{35}SO_4$ in serum-free medium and immunoprecipitated from the medium using a rabbit polyclonal anti-fibrinogen antiserum (Accurate Chemical and Scientific Corp., Westbury, N.Y.) as described previously (10). The amount of fibrinogen secreted during the labeling was determined using an ELISA described previously (10). Identical amounts of radiolabeled fibrinogens (300 ng) were resolved by SDS-polyacrylamide gel electrophoresis on 10% gels under reducing conditions (36) and exposed to X-ray film.

Thrombin/γ' Peptide Binding Assay. To quantitate the binding of thrombin to the γ' chain carboxyl terminus, 50 nM VRPE-HPAETE-Y ($PO_3$)-DSL-Y ($PO_3$)—PEDDL (SEQ ID NO: 10) peptide (Research Genetics), corresponding to the carboxyl terminal twenty amino acids of the γ' chain, was labeled for 1 hour at 37° C. with a 5-fold molar excess of fluorescein succinimidyl ester (PanVera) in 100 mM potassium phosphate, pH 7.0 as per the manufacturer's protocol. Unreacted fluorescein succinimidyl ester was reacted with 100 mM Tris, pH 8.0 for 30 minutes and removed by desalting the fluoresceinated peptide on Sephadex G-15 in 137 mM NaCl/2.7 mM KCl/10 mM HEPES, pH 7.4. 2 nM fluoresceinated peptide was incubated with the indicated concentrations of thrombin for 30 seconds at 22° C. in 50 μg/ml BSA/137 mM NaCl/2.7 mM KCl/10 mM HEPES, pH 7.4. Fluorescence polarization was measured following excitation at 488 nm and emission at 535 nm. The data are fit to the equation:

$$y=x/(b+x)$$

where y is fit to x, using "x" as the concentration of thrombin and "b" as the $K_d$.

Competitive binding assays were performed by incubating 2 nM fluoresceinated peptide with 2 μM α-thrombin in the presence of the indicated concentrations of competing ligand. Fluorescence polarization was measured following excitation at 488 nm and emission at 535 nm.

Thrombin Inhibition Assay. 1.37 nM α-thrombin in 2.9 ml 227 mM NaCl/50 mM Tris HCl pH 8.3/1 mg/ml BSA was reacted for 15 minutes at 22° C. with 13.7 nM ATIII (Enzyme Research Laboratories, South Bend, Ind.) in the presence of 0-1.0 mM γ' peptide. In some experiments, 0.33 μM heparin (Sigma) was included in the reaction. The inhibition reaction was terminated by the addition of 0.3 ml of a vast molar excess of substrate, 1.25 mg/ml Chromozym TH (Boehringer Mannheim, Indianapolis, Ind.), and the remaining thrombin activity was subsequently measured by monitoring the absorbance at 405 nm for 15 minutes at 22° C.

Results

Two Tyrosine Residues in the γ' Chain Are Sulfated. The human γ' chain contains tyrosine O-sulfate residues, whereas the γA chain does not (10). Since the γ' chain differs from the γA chain only in its carboxyl terminal 20 amino acids, it has been assumed that the sulfated residues are within this 20 amino acid sequence, although the addition of the γ' sequence could also induce conformational changes in the γ chain that expose new sites for sulfation upstream of the carboxyl terminus. However, earlier studies demonstrated that the γ' chain $^{35}$S-labeled tyrosine O-sulfate residues were rapidly released by carboxypeptidase Y digestion (10), consistent with a carboxyl terminal location. The carboxyl terminus of the γ' chain contains two potential sites for tyrosine sulfation at positions γ' Y418 and γ' Y422. Analysis of the γ' chain by mass spectrometry indicated that the observed mass was 151 Da greater than the mass predicted by the primary sequence, assuming monosialyation at the γ' chain glycosylation site (6), and was roughly the same as the increase in mass predicted by sulfation at two tyrosine residues (160 Da). However, no direct evidence of sulfation at γ' Y418 or γ' Y422 was presented. Furthermore, in both bovine and rat fibrinogen, the γ' chain terminates at the equivalent of γ' 420, prior to γ'Y422 (37, 38). The rat γ' chain does, however, contain sulfotyrosine (39). Therefore, in order to determine if these tyrosine residues are indeed sulfated, recombinant fibrinogen molecules were synthesized with tyrosine to phenylalanine substitutions at positions γ' Y418 and/or γ' Y422 (FIG. 1).

FIG. 1 shows the carboxyl terminal sequences starting at amino acid 408 of the major isoform of the γ chain, γA, and the minor isoform, γ'. Also shown are sequences of recombinant fibrinogen mutants with Tyr→Phe substitutions that eliminate potential sulfation/phosphorylation sites at γ'Y418 and γ' Y422.

Transfected BHK cells expressing the mutant fibrinogens were incubated with $^{35}SO_4$ to label the tyrosine O-sulfate moieties, and the recombinant fibrinogens were immunoprecipitated from the conditioned medium and analyzed by gel electrophoresis. FIG. 2 shows that no radiolabeled bands were observed in the immunoprecipitates from the non-transfected BHK parental cells (lane 1), nor from BHK cells transfected with cDNAs encoding γA/γA fibrinogen (lane 2). However, immunoprecipitates from cells transfected with cDNAs encoding γ'/γ' fibrinogen showed a radiolabeled band that co-migrated with the γ' chain (lane 3). The intensity of this band was reduced substantially in the γ' Y418F mutant (lane 4), with a somewhat lesser reduction in the γ' Y422F mutant (lane 5). No band was visible in the γ' Y418F/Y422F double mutant (lane 6), confirming that these are the only tyrosine residues in human fibrinogen that are sulfated significantly.

Although the reduction in tyrosine sulfation was greater in the γ'Y418F mutant than the γ'Y422F mutant, this should not necessarily be interpreted to mean that γ'Y418 is sulfated to a greater extent than γ'Y422. Removal of the negative charge at position γ'Y418 affects the consensus sequence for tyrosine sulfation at γ' 422; removal of negatively charged amino acids at the −4 position has been shown to increase the $K_m$ for tyrosylprotein sulfotransferase reactions (40). Preliminary studies suggest that both tyrosine residues may be fully sulfated (41), consistent with the data obtained by mass spectrometry (6) and the present results. However, irrespective of the stoichiometry of sulfation, these data show that both the 'Y418 and γ'Y422 residues can be sulfated, and that no other sulfation sites exist in the γ' chain.

Figure 3:
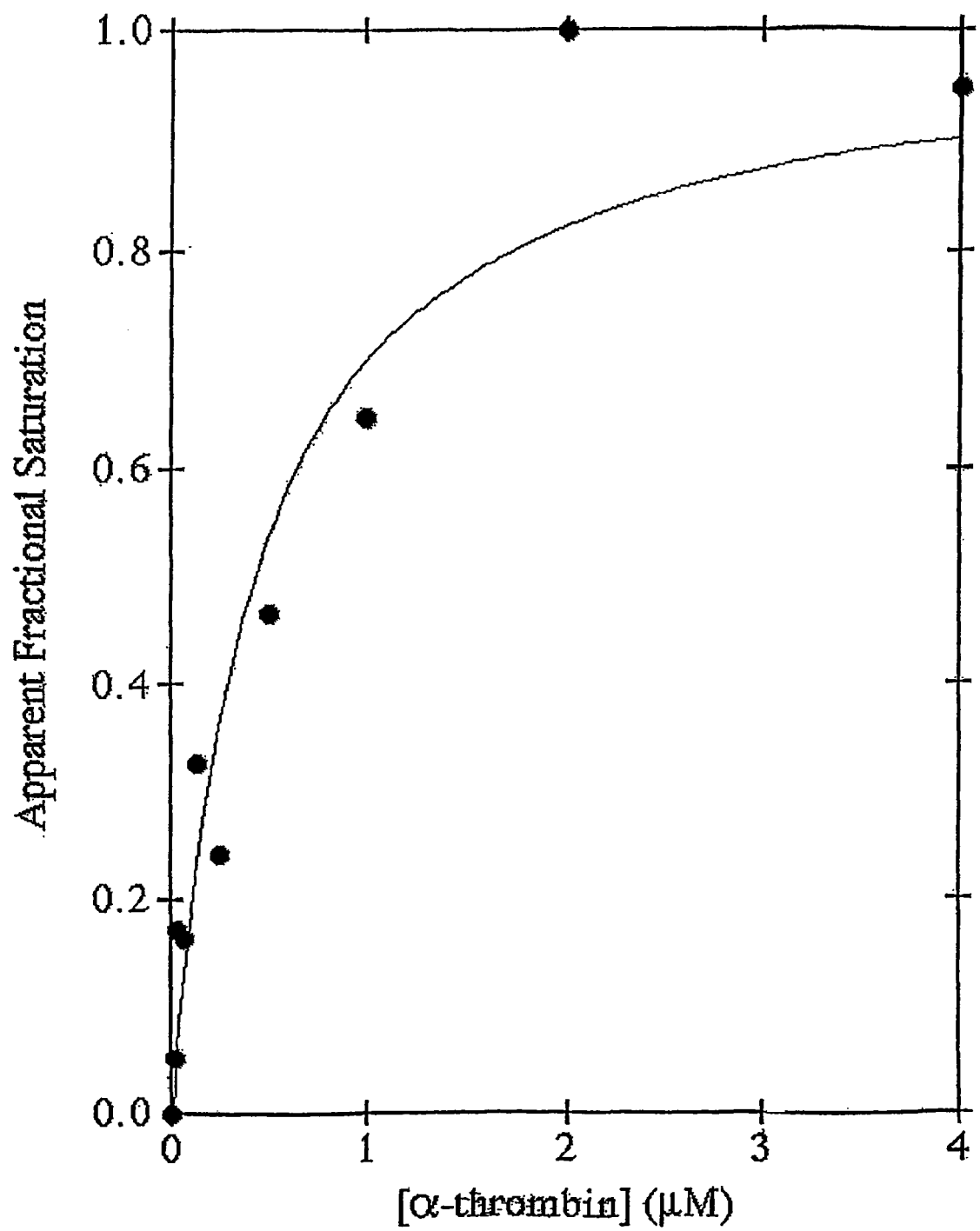
FIG. 3 shows binding of α-thrombin to fluoresceinated γ' 408-427 peptide.

The γ' Peptide Binds to Thrombin Exosite II. The chemical synthesis of peptides containing sulfotyrosine residues is problematic due to the acid lability of the sulfate moieties (6), and extremely low yields are obtained. In a previous study, γ' peptides were sulfated at γ'Y418 and 422 by chemical modification, but this required the substitution of γ' T416 and γ' S420 with Val residues to prevent their sulfation as well (6). Therefore, for the present studies, a twenty amino acid peptide corresponding to the carboxyl terminus of the γ' chain was synthesized, VRPEHPAETE-Y($PO_3$)-DSL-Y($PO_3$)—PEDDL (SEQ ID NO: 10), in which acid-stable phosphotyrosine residues were substituted for sulfotyrosine residues at γ'Y418 and γ'Y422. This eliminated the need to introduce the γ' T416V and γ' S420V mutations into the γ' peptide. Tyrosine phosphorylation has been used successfully as a substitute for tyrosine sulfation in recombinant hirudin expressed in E. coli, where it restores wild-type binding activity towards thrombin (29). The γ' peptide was labeled with fluorescein at the amino terminus and tested for its ability to bind thrombin by monitoring the change in fluorescence polarization. FIG. 3 shows a significant, dose-dependent increase in fluorescence polarization of the labeled γ' peptide as thrombin was added, indicative of direct binding between the γ' peptide and thrombin. Furthermore, the binding was saturable, with a $K_d$=0.43±0.08 μM, similar in magnitude to the $K_d$ of 0.20 μM determined previously for thrombin binding to γA/γ fibrin (3). These results demonstrate that thrombin can bind directly to the tyrosine phosphorylated γ' carboxyl terminal twenty amino acid peptide, with a similar affinity to γA/γ fibrin.

Figure 4:
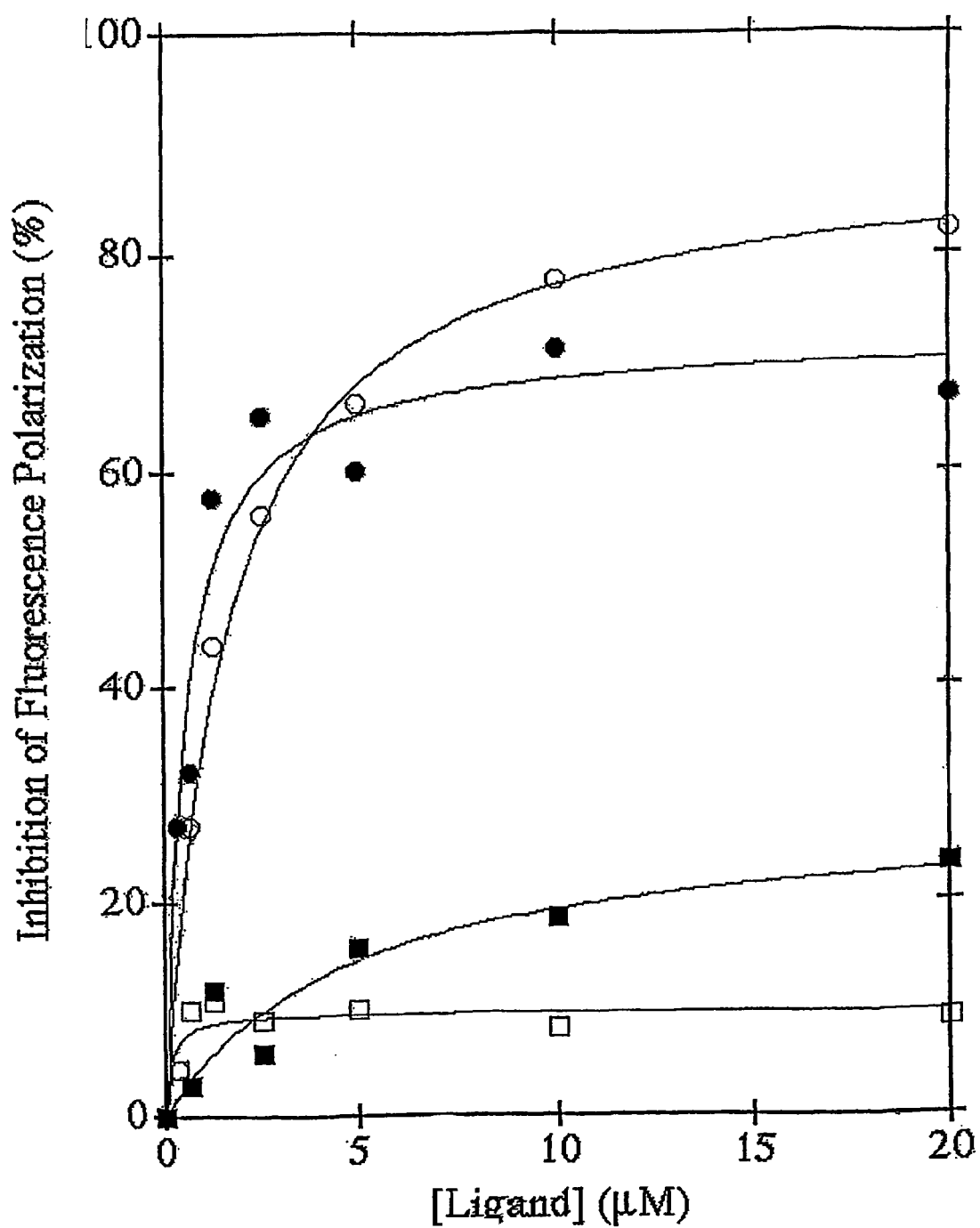
FIG. 4 shows inhibition of α-thrombin binding to fluoresceinated γ' 408-427 peptide by heparin (○), and hirudin (53-65 (■) and 54-65 (□) peptides, and unlabeled γ' 408-427 (•).
Figure 5:
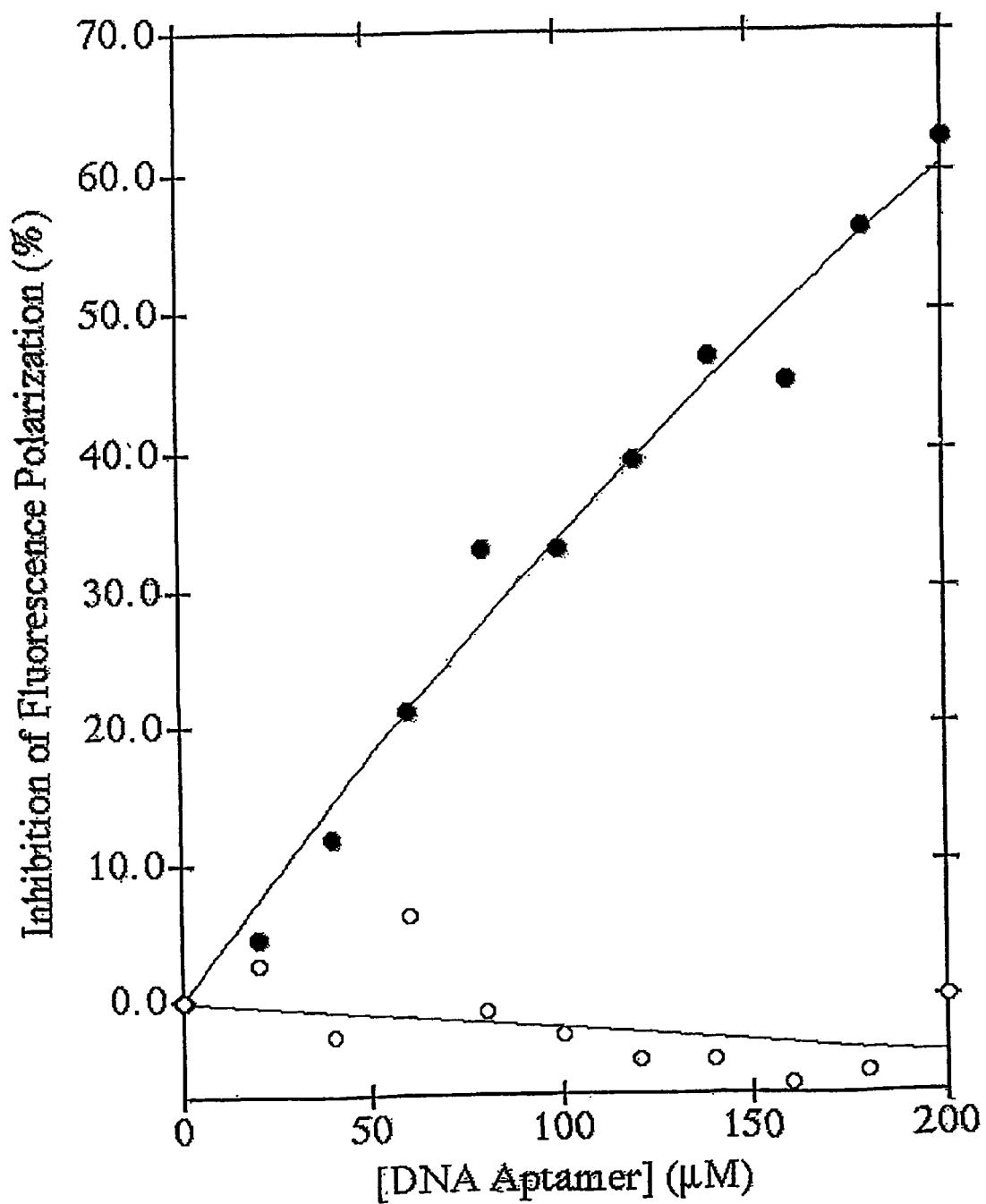
FIG. 5 shows inhibition of •-thrombin binding to fluoresceinated •' 408-427 peptide by DNA aptamers (HD1 (•) and HD22 (•)) directed against exosites I and II.
Figure 6:
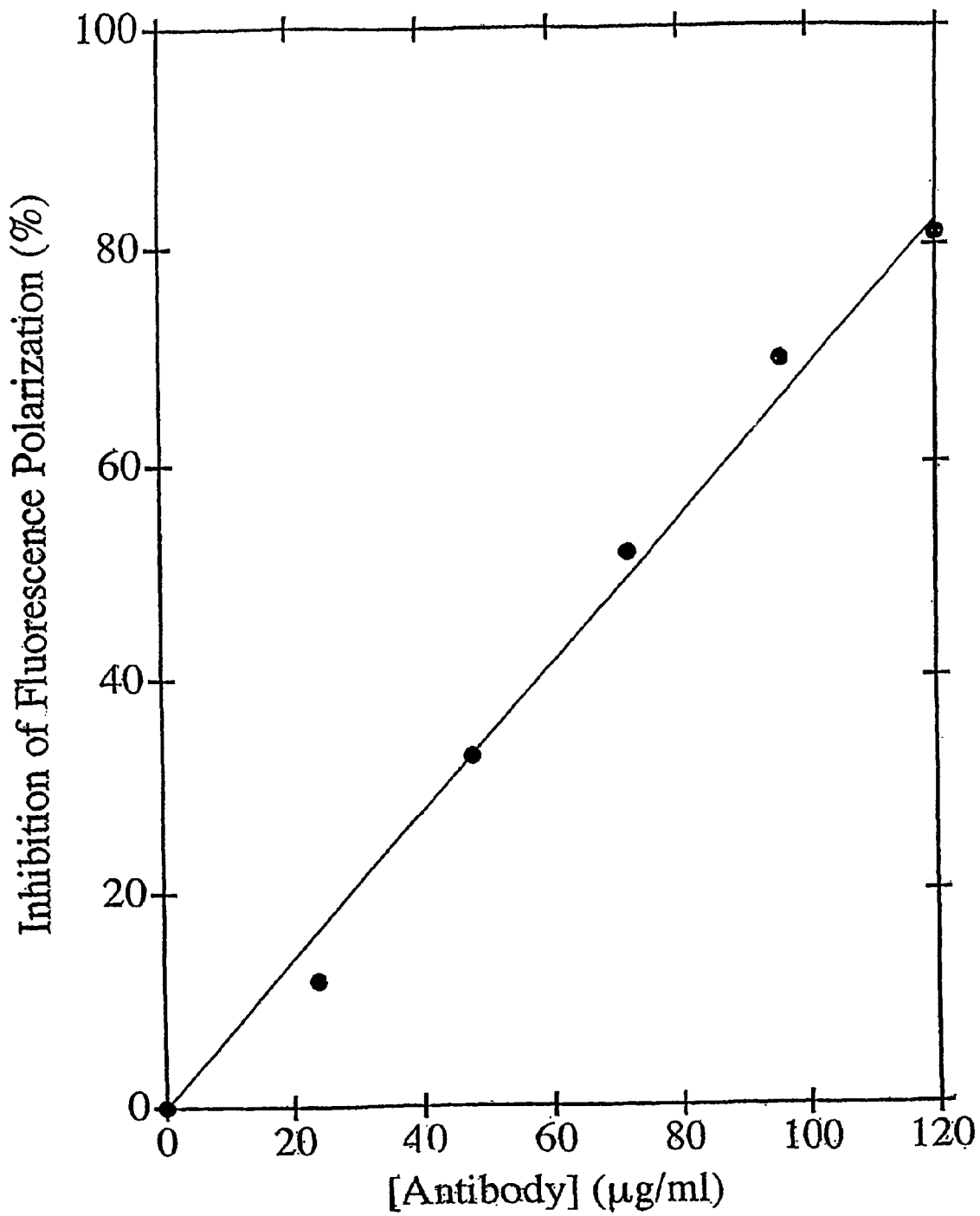
FIG. 6 shows inhibition of α-thrombin binding to fluoresceinated γ' 408-427 peptide by a monoclonal antibody directed against exosite II.

To map the binding site of the γ' peptide on thrombin, competitive binding assays were performed using ligands for exosite I and II. Hirudin peptides 53-65 (■) and 54-65 (□) showed only weak inhibition of γ' peptide binding to thrombin (FIG. 4), and it was not possible to obtain a statistically significant $K_i$ value for either peptide. In contrast, heparin (○) was a strong competitor for the γ' peptide, with a $K_i$ value of 1.6±0.31 μM, based on an average molecular weight of 15 kDa for unfractionated heparin. Competition with the unlabeled γ' 408-427 (●) is shown for comparison. These results are consistent with the notion that the γ' peptide binds primarily to exosite II, rather than exosite I. However, since heparin is a heterogeneous mixture of species, exosite-specific DNA aptamers were used to confirm the identity of exosite II as the binding site for the γ' peptide. DNA aptamers HD1 and HD22 that bind preferentially to exosites I or II, respectively (27), were used as competing ligands for the γ' peptide. As shown in FIG. 5, HD22 (●) was a more potent competitor than HD1 (○), confirming the results in FIG. 4 that the γ' peptide binds primarily to exosite II. In addition, a monoclonal antibody that blocks exosite II specifically (34) was used as a competing ligand for the γ' peptide (FIG. 6). As with heparin and HD22, this antibody blocked binding of the γ' peptide to thrombin in a dose-dependent manner, indicating that the γ' peptide binds to exosite II.

Figure 7:
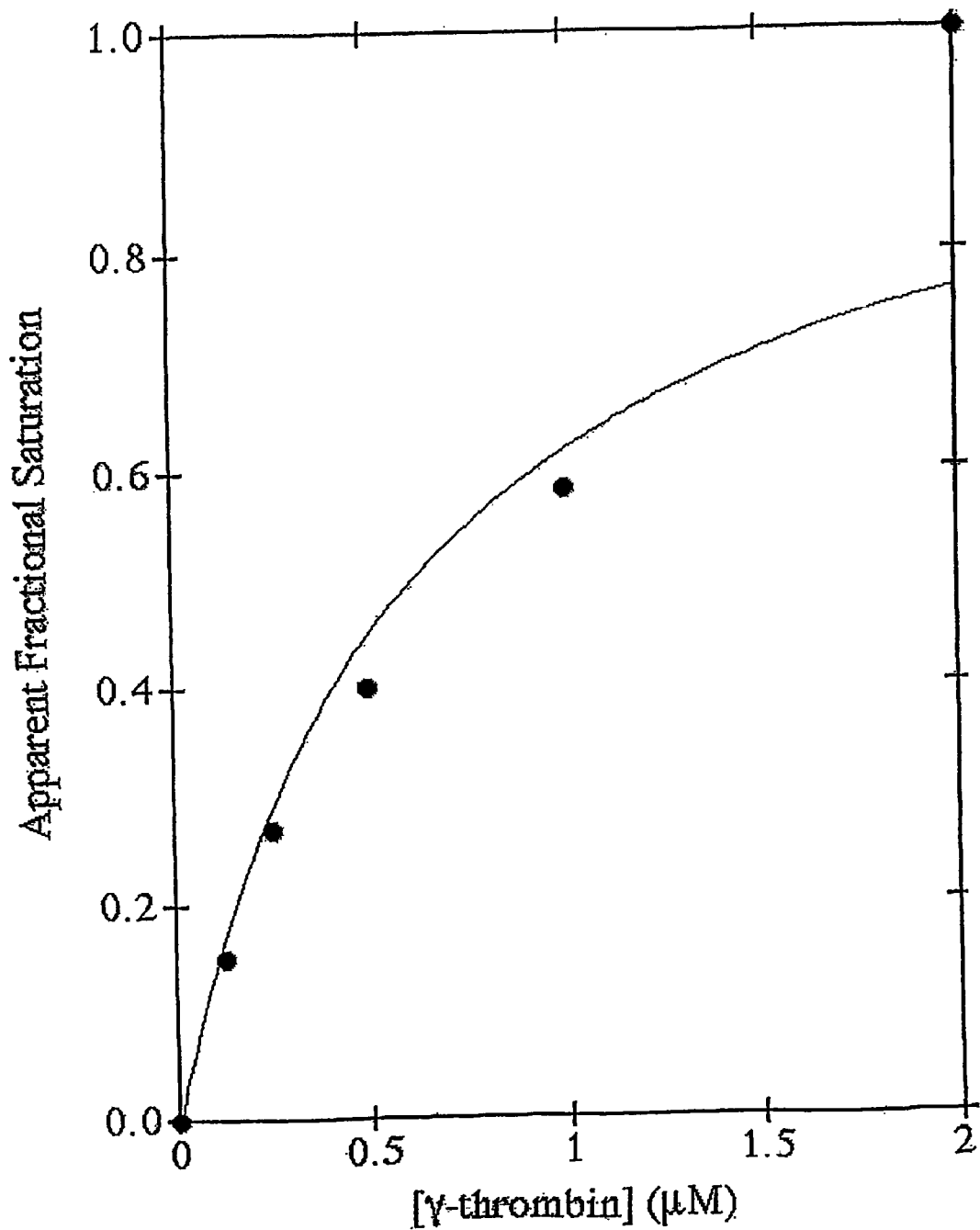
FIG. 7 shows binding of γ-thrombin to fluoresceinated γ' 408-427 peptide.

To determine if the γ' peptide binds exosite II, rather than exosite I, binding of the γ' peptide to γ-thrombin was examined. γ-thrombin was chosen for these studies because it is a proteolyzed product of α-thrombin in which exosite I fails to bind fibrinogen or hirudin (42). In fact, the $K_d$ for γ-thrombin was of similar magnitude as that for α-thrombin, 0.61±0.15 μM (FIG. 7), thus providing further evidence that the γ' peptide binds exosite II. The observation that exosite I did not bind the γ' chain is also consistent with previous reports that hirudin-based thrombin inhibitors fail to displace $^{125}$I-labeled thrombin from clots (15).

Figure 8:
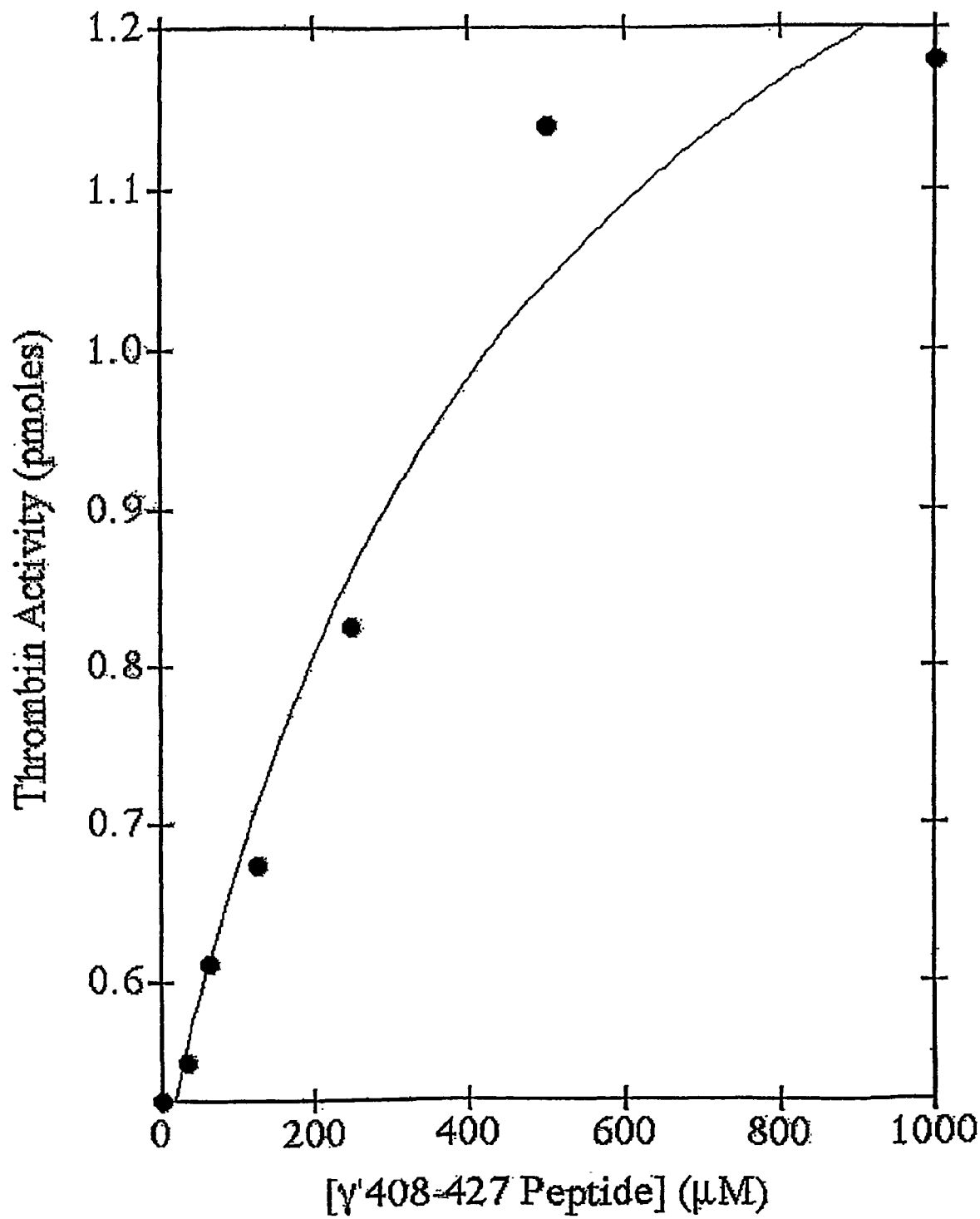
FIG. 8 shows inhibition of heparin cofactor activity by γ' 408-427 peptide.

The γ' Chain Carboxyl Terminus is a Heparin Antagonist. Since exosite II is a heparin binding site, the γ' chain could potentially antagonize heparin cofactor activity towards thrombin. The effect of the γ' 408-427 peptide on heparin acceleration of thrombin inhibition by ATIII was therefore investigated. For these studies, the tyrosine phosphorylated mimetic of the γ' peptide carboxyl terminal peptide VRPEH-PAETEYDSLYPEDDL (SEQ ID NO: 11) was again used. In prior studies by others, the nonphosphorylated form of this peptide showed direct inhibitory activity towards thrombin, albeit with a relatively high $K_i$ of 0.13 mM (43). In contrast, the tyrosine phosphorylated γ' 408-427 peptide was not directly inhibitory at concentrations up to 1 mM (data not shown). However, the peptide antagonized heparin's acceleration of thrombin inhibition by ATIII in a dose-dependent manner (FIG. 8). In this assay, the concentrations of thrombin and ATIII were adjusted so that approximately half (2.1 pmoles) of the total thrombin (4.4 pmoles) was inhibited in 15 minutes in the absence of heparin, and the majority of the thrombin (3.8 pmoles) was inhibited in the presence of 0.33 μM heparin. The γ' 408-427 peptide antagonized the accelerative activity of heparin in a dose-dependent manner, suggesting that binding of the γ' peptide to exosite II blocked heparin binding, preventing heparin from accelerating thrombin inhibition by ATIII. These results provide a possible mechanism for the heparin resistance of fibrin clot-bound thrombin.

Figure 9:
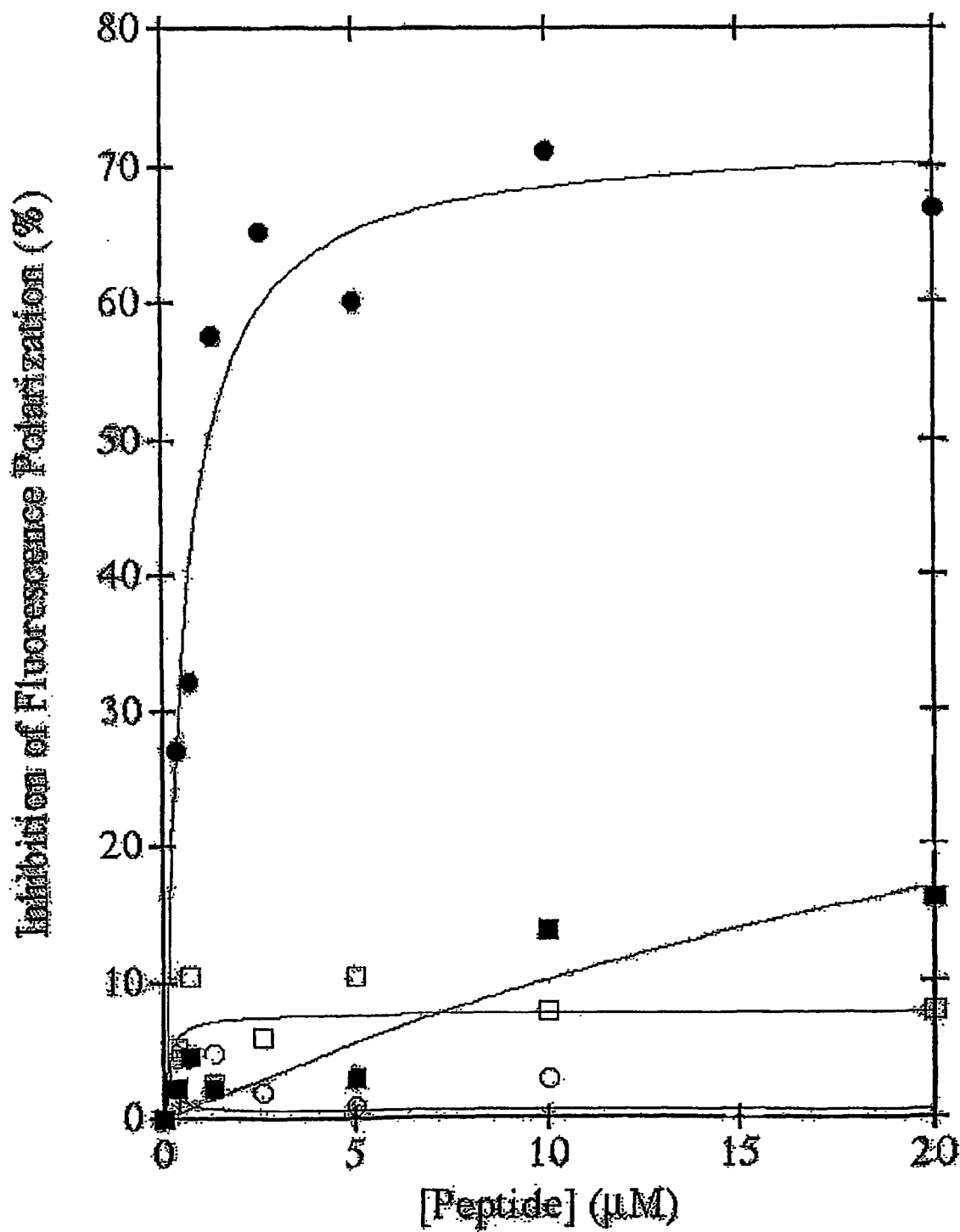
FIG. 9 shows inhibition of •-thrombin binding to fluoresceinated •' 408-427 phosphorylated peptide by •' 408-427 mutant peptides (•'Y(PO$_3$)418 (•), •'Y(PO$_3$)422 (•), •'Y(PO$_1$) 418/Y(PO$_3$)422 (•), and nonphosphorylated peptide (•)).

Negative Charges on γ' Y418 and γ' Y422 Are Required for Maximum Thrombin Binding. In order to determine the contribution of the negative charges at γ' Y418 and γ' Y422 to thrombin binding, twenty amino acid peptides were synthesized with phosphotyrosine at one or the other position. FIG. 9 shows that only the doubly phosphorylated peptide was able to compete effectively for binding to thrombin. The peptide containing γ' Y(PO$_3$)418 (■) appeared to be slightly more effective than the peptide containing γ'Y(PO$_3$)422 (□), but it was not possible to obtain a statistically significant Ki value for either peptide. In contrast, a Ki value of 0.52±0.14 μM was obtained for the doubly phosphorylated peptide (●), similar to the Kd determined previously by direct binding assays. The nonphosphorylated peptide (○) was completely inactive in this competitive binding assay. These results indicate that negative charges at both γ'Y418 and γ'Y422 are necessary for maximum binding to thrombin.

The necessity for negative charges at both γ' Y418 and γ' Y422 for maximal thrombin binding is somewhat surprising in light of the fact that γ' Y422 is not conserved in γ' chains found in other species. In both bovine and rat fibrinogen, the γ' chain terminates at the equivalent of γ' 420, prior to γ'Y422. The rat γ' chain does, however, contain sulfotyrosine, although it is not known if sulfotyrosine is present at the equivalent position of human γ'Y418.

Serial Deletion of the γ' Peptide Decreases Binding to Thrombin.

Figure 10:
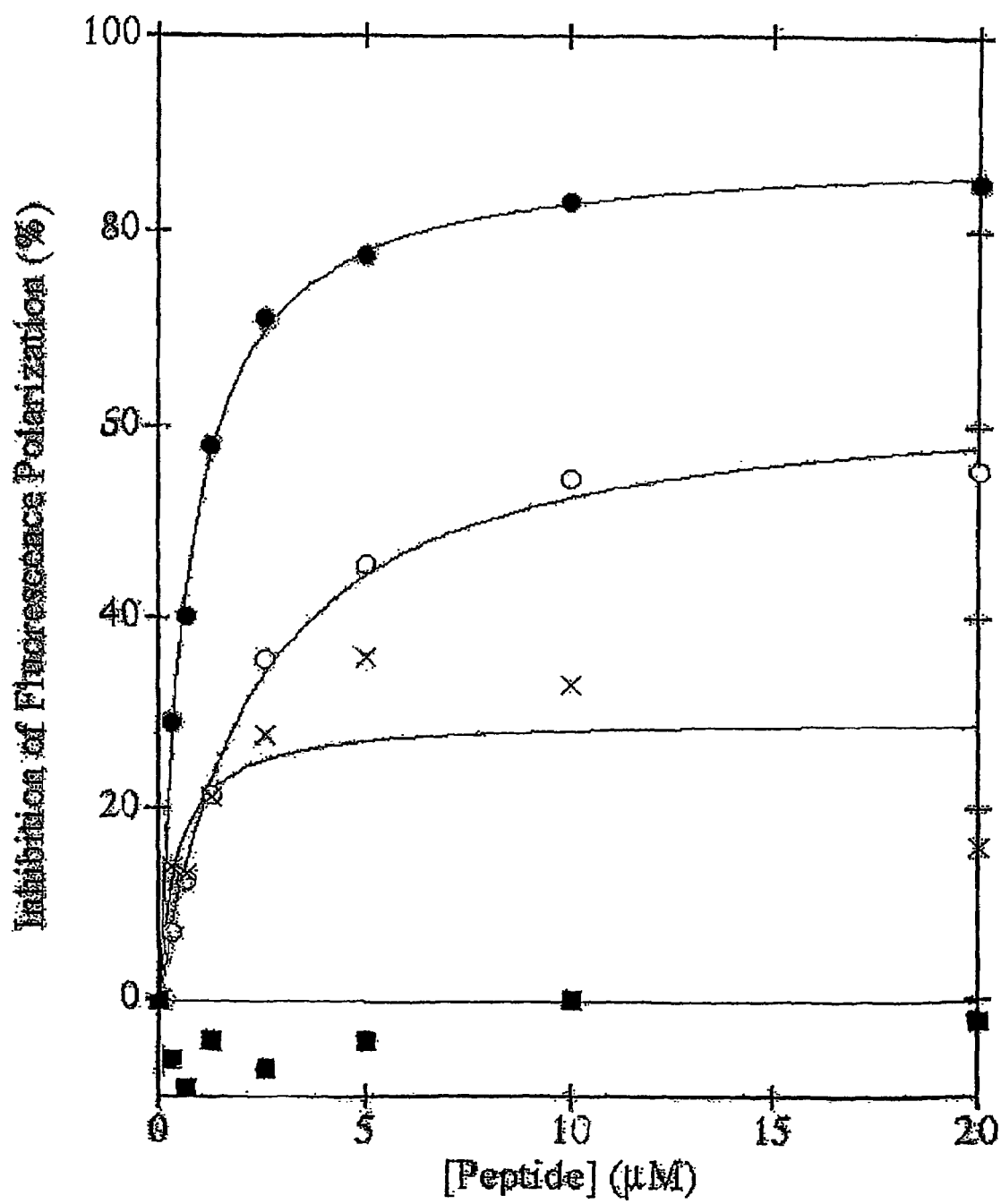
FIG. 10 shows inhibition of α-thrombin binding to fluoresceinated γ' 408-427 phosphorylated peptide by truncated γ' 408-427 peptides (peptide 411-427 (•), peptide 414-427 (○), peptide 408-424 (X), and peptide 417-427 (□)).

To determine the minimum region of the γ' necessary for thrombin binding, serial deletions of the γ' peptide were tested for their ability to compete for thrombin binding (FIG. 10). Peptides were synthesized with phosphotyrosine at both positions 418 and 422. Amino-terminal deletion peptide 411-427 (●) was similar to the 408-427 peptide in competing for thrombin binding. In contrast, the amino-terminal deletion peptide 414-427 (○) had a lower affinity, as did the carboxyl-terminal deletion peptide 408-424 (X). The amino-terminal deletion peptide 417-427 (□) was completely inactive. These data indicate that the region of the γ' chain from 414-417 contain residues that are critical for thrombin binding. In addition, the region from 411-414 contributes to γ' binding affinity, as does the carboxyl terminus from 424-427.

Discussion

Clot-bound thrombin plays a significant role in thrombus growth and in restenosis following thrombolytic therapy, even when therapeutic levels of heparin are administered (14, 15). The data presented here provide a plausible mechanistic explanation for these observations. γA/γ fibrin has a high affinity binding site for thrombin at the carboxyl terminus of the γ' chain (3, 6). The cognate binding site on thrombin is shown in the present study to be anion-binding exosite II, a site known to bind heparin (24, 25). Therefore, when thrombin binds to the γ' chain of fibrinogen via exosite II, this leaves exosite I and the active site accessible to substrates, while simultaneously blocking heparin binding to exosite II. This may explain why fibrin-bound thrombin can retain enzymatic activity and amplify coagulation locally, thereby causing thrombus growth, and why fibrin-bound thrombin is resistant to heparin.

Figure 11:
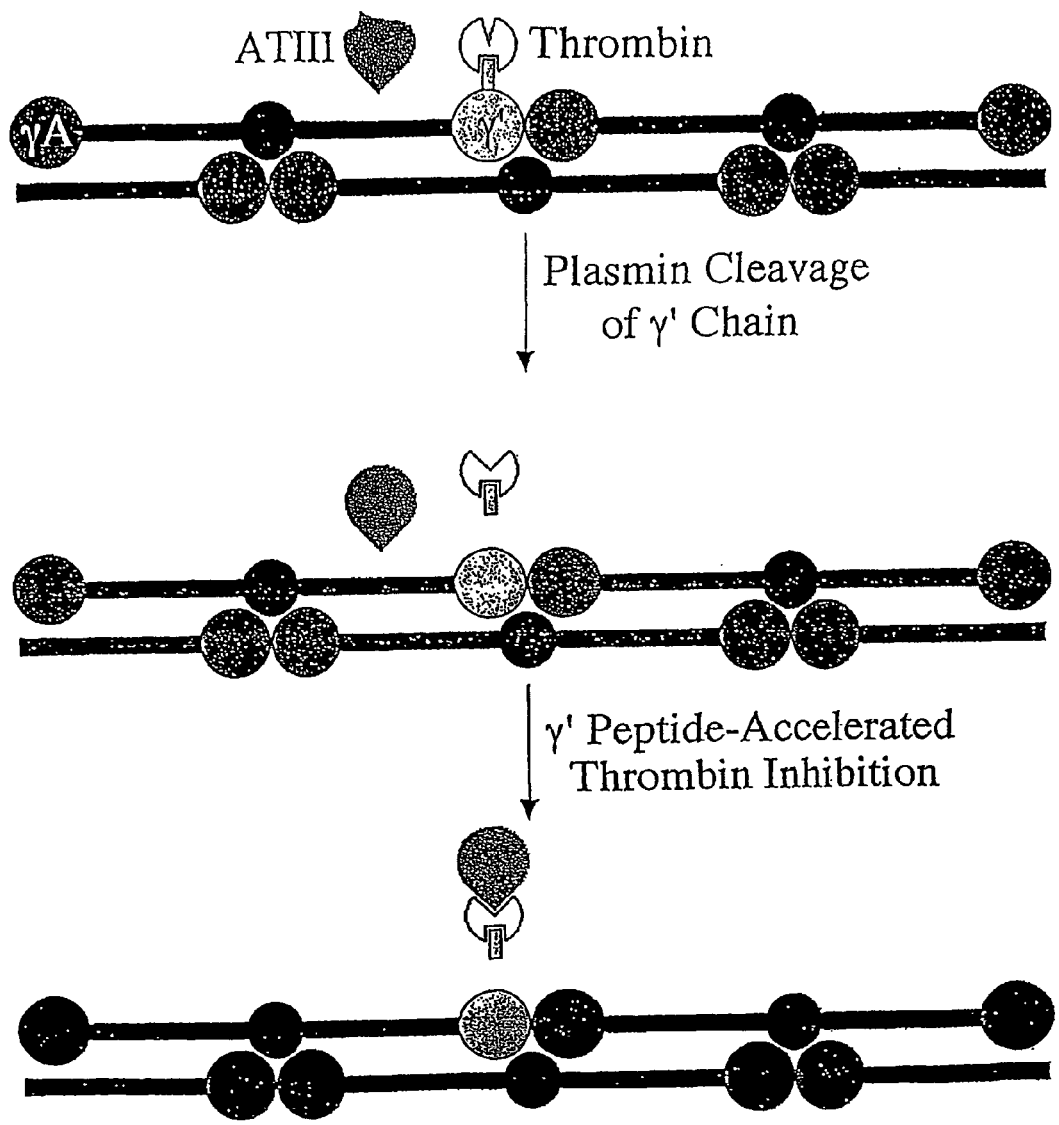
FIG. 11 is a schematic depicting thrombin/γ' chain interactions during coagulation and fibrinolysis.

These data extend previous observations that the low affinity interaction of thrombin with fibrin is mediated by exosite I (44, 45, 46), whereas high affinity binding to γ' (3, 6) is shown here to involve exosite II. In binding studies of thrombin to fibrin, the large number of low affinity sites may mask the minor component of high affinity exosite II-mediated binding to the γ' chain, particularly because only a minority of fibrinogen molecules contain the γ' chain. Since the concentration of γA/γ fibrinogen is estimated to constitute about 14% of the total fibrinogen in plasma (9), with an average concentration of about 300 mg/dl (49), the concentration of γA/γ fibrinogen in plasma is likely to be about 0.88 μM. In addition, the local concentration of γA/γ fibrin in the solid-phase clot will be much higher than the concentration of soluble γA/γ fibrinogen. At these concentrations, a considerable amount of the free thrombin generated in plasma could be bound to γA/γ fibrin were it not for competition with other blood components such as ATIII, heparin cofactor II, platelet GPIb, and endothelial heparan sulfate. In addition, the fact that the γ' carboxyl terminus is cleaved by plasmin (13) provides a potential mechanism for both removing clot-bound thrombin during fibrinolysis and increasing the rate of thrombin inhibition by ATIII (FIG. 11). Such a mechanism could prevent further recruitment of fibrin into the clot when the fibrinolytic cascade is activated.

As shown in the model depicted in FIG. 11, thrombin is initially generated and cleaves fibrinogen to form fibrin. Active thrombin binds through exosite II to the γ' chain in γA/γ fibrin, where it converts more fibrinogen to fibrin, thereby causing thrombus growth. Thrombin bound to the γ' chain is also heparin-resistant, since exosite II is blocked. The formation of fibrin activates the fibrinolytic cascade, resulting in plasmin cleavage of the γ' chain. The released γ' 410-427 peptide binds to thrombin, possibly displacing residual clot-bound thrombin and enhancing thrombin's rate of inactivation by ATIII.

The findings presented herein suggest a potential therapeutic use for γ' 410-427 peptide. The plasmin-cleaved γ' peptide may displace bound thrombin from the high affinity thrombin binding site, and thus serve as an anticoagulant. In addition, the physical nature of the peptide makes it unlikely to induce an immune response, due both to its identity with a normal plasmin breakdown product of human γA/γ fibrin and due to its small size.

EXAMPLE II

Synthetic Anti-Thrombotic Peptide Analogs

Recombinant DNA technologies provide the means to generate synthetic modified γ' peptides having the same or altered biological activities. Using the one letter amino acid code, the following substitutions can be made in the γ' peptides of the invention.

```
V R P E H P A E T E Y D S L Y P E D D L
I K   D       D V D   E A I     D E E I
L                         V           V;
``` wherein the tyrosines may be phospho- or sulfo-tyrosine (SEQ ID NO: 56). It is also within the scope of the invention to modify the peptide to contain a plurality of sulfation signals. Exemplary consensus sequences for this purpose include EEPEYGE (SEQ ID NO: 12) and EEFEEAYIP SEQ ID NO: 13). Such sequences may be added as direct repeats. Approximately 3-12 direct repeats may be added at either the carboxyl or amino terminus or within the γ' peptide sequence described herein. Other peptides within the scope of the invention act to modulate coagulation and can contain 1, 2, 3, 4, or 5, amino acid insertions or deletions.

An exemplary synthetic anti-thrombotic precursor peptide of the invention has the following generic structure:

γ signal sequence-tag sequence-spacer sequence--2, -1 cleavage site-γ' 18-mer

The signal sequence may be any signal sequence which facilitates trans Golgi processing and secretion; the tag sequence may be any amino acid epitope which facilitates purification and/or detection of the recombinant peptide. Such sequences include without limitation, a histidine tag, a FLAG epitope, a c-myc epitope and the like; the spacer sequence may be any inert amino acid sequence, e.g., a polyalanine sequence; −2, −1 positions refer to an artificial cleavage site. Such sites include, for example a trypsin cleavage site, or an enterokinase site. A natural plasmin cleavage site occurs in the γ' chain between the R residue at −1 and the P residue at +1. Upon cleavage of the synthetic peptide, the γ' 18 mer bioactive peptide of the invention is released. As mentioned, the γ' 18 mer may be substituted with any of the amino acids shown above.

A series of representative synthetic anticoagulation peptide precursors is set forth below:

MSWSLHPRNLILYFYALLFLSSTCVA-[γ signal sequence]-HHHHHH-[6× His tag]-AAAAAAAAAAAAAAAA [spacer]-VR-[trypsin cleavage site]-PEHPAETE(sulfoY)DSL(sulfoY)PEDDL (SEQ ID NO: 14);

MFSMRIVCLVLSVVGTAWT-[α signal sequence]-MDYKDDDDK-[FLAG tag/enterokinase cleavage site]-PEHPAETE(sulfoY)DSL(sulfoY)PEDDL(SEQ ID NO: 15); and MKHLLLLLLCVFLVKS-[β signal sequence]-EQKLISEEDL-[c-myc tag]-EXXYXQS-[TEV protease cleavage site]-PEHPAETE(sulfoY)DSL(sulfoY)PEDDL (SEQ ID NO: 16).

Each of the last two synthetic peptides may optionally contain a polyalanine spacer sequence between the cleavage site and the bioactive peptides. Finally, while sulfation of the tyrosine residues is shown above, phosphorylation of the synthetic peptides at tyrosine residues is also within the scope of the invention.

The γ' peptides of the invention may be expressed by recombinant means in a variety of expression systems. These include bacterial, yeast, mammalian cell line and insect cell line based system. Such systems also enable production of the peptide of the invention in large scale fermenters.

The anti-thrombotic peptides of the invention possess anti-coagulant activity and anti-platelet activity. In addition, such peptides should release clot-bound thrombin that is bound to the γ' chain of the γA/γ fibrin. This event should further enhance thrombin inhibition, since clot-bound fibrin is resistant to inactivation by anti-thrombin III. Furthermore, unlike heparin, such synthetic peptides should be non-immunogenic as they are chemically similar to naturally-occurring fragments of γA/γ fibrin. This feature should prevent the occurrence of heparin-induced thrombocytopenia, a potentially fatal reaction to heparin infusion which occurs in 1-3% of individuals receiving such treatment.

EXAMPLE III

The Fibrinogen γ' Peptide has Anti-Coagulation Activity in Human, Rat, and Mouse Plasma The following protocols are provided to facilitate the practice of the methods of the present invention.

Activated Partial Thromboplastin Time (aPTT) Assay. This anti-coagulation assay was chosen for testing the γ' peptides due to its sensitivity to heparin-like compounds, its ease of use, and the ability to automate the procedure. An MLA 1600 instrument (Organon Teknika) was used to quantitate the effect of the γ' peptides on the aPTT, using the manufacturer's protocol. Briefly, 0-1 mM γ' peptides or 0-10 units/ml unfractionated heparin was added to 50 μl of normal reference plasma (Ortho) and manually loaded into the MLA 1600. The MLA 1600 added SynthASil aPTT reagent (Ortho) to initiate clotting, and clot formation was monitored spectrophotometrically for 106 seconds. The results of these analyses demonstrated the effect of the γ' peptides on the aPTT.

Prothrombin Time/International Normalized Ratio Assay. This clotting assay is less sensitive to heparin than the aPTT, and may be used to determine if a γ' peptide is capable of prolonging the prothrombin time (PT) to the same extent as the 3 aPTT. One-stage PT assays may be performed using an MLA 1600 instrument according to the manufacturer's protocol. Briefly, 0-1 mM γ' peptide or scrambled peptide or 0-10 units/ml unfractionated heparin may be added to 50 μl of normal reference plasma (Ortho) and manually loaded into the MLA 1600. The MLA 1600 may be used to add recombinant thromboplastin (Recombiplastin, Ortho) to initiate clotting, and clot formation monitored spectrophotometrically for 106 seconds. If a clot is not generated within 106 seconds, the MLA will automatically extend the observation time to 212 seconds.

The International Normalized Ratio (INR) for a sample may be calculated using the known International Sensitivity Index (ISI) for the recombinant thromboplastin (typically 0.99). The equation INR=Patient PT (seconds)ISI/Normal PT (seconds) is used by the instrument to calculate the INR. The results of this analysis may be used to demonstrate the effect of the γ' peptide on the PT.

Reptilase Time Assays. The reptilase time may be used as a control assay to examine the effects of a γ' peptide. This assay is insensitive to thrombin inhibitors, since reptilase is used to clot fibrinogen rather than thrombin. An LA STA instrument (Diagnostica Stago) may be used to quantitate the effect of the γ' peptide on the RVV, using the manufacturer's protocol. Briefly, 0-1 mM γ' peptide or scrambled peptide or 0-10 units/ml unfractionated heparin may be added to 1 ml of normal reference plasma (DVVtroll) and loaded into the LA STA. The LA STA may be used to add Reptilase ST reagent (American Diagnostica) to initiate clotting, and clot formation monitored spectrophotometrically for 65 seconds. The results of this analysis may be used to advantage to demonstrate the effect of the γ' peptide on the reptilase time.

Platelet Aggregometzy Assays. This assay may be used to test the effects of a γ' peptide on platelet aggregation in platelet-rich plasma. The activity of a γ' peptide may be assayed in the presence or absence of epinephrine, ADP, collagen, ristocetin, arachidonic acid, and thrombin. A PAP-4 platelet aggregometer (Bio/Data) was used to quantitate the effect of the γ' peptide on platelet aggregation, using the manufacturer's protocol. Briefly, normal reference platelet-rich plasma from established control groups were generated by centrifugation of whole blood collected in 1/10 volume 0.294% sodium citrate/0.210% citric acid. Blood was centrifuged for 10 minutes at 1,000×g, to isolate the supernatant of platelet-rich plasma. All experiments were performed within 2 hours of the blood draw. 0-1 mM γ' peptide or scrambled peptide or 0-10 units/ml unfractionated heparin was added to 450 μl of platelet-rich plasma and loaded into siliconized cuvettes. 50 μl of agonist was added and the absorbance monitored for 6 minutes. The agonists used were 10 μg/ml epinephrine (American Reagent Laboratories), 2 μM ADP (Sigma), 0.5 mg/ml arachidonic acid (Bio/Data), or 0.2 units/ml thrombin. The presence or absence of a bi-phasic response may be determined, which is of particular significance in the presence of epinephrine, ADP, and ristocetin. The length of the lag phase may be determined, which is especially relevant in the presence of collagen.

PFA-100 Assays. The effect of the γ' peptide on platelet function may also be assessed using a Platelet Function Analyzer (PFA-100™, Dade Behring). The PFA-100 instrument measures the closure time of a capillary tube containing whole blood. This assay may be used to advantage to examine the effect of γ' peptide on platelet function in whole blood in the presence of either of the platelet agonists epinephrine or ADP. Briefly, 0-1 mM γ' peptide or scrambled peptide or 0-10 units/ml unfractionated heparin may be added to 800 μl of normal reference whole blood from an established control group and loaded into the PFA-100 to measure the closure time. Platelet function may be tested using both a collagen/epinephrine cartridge and a collagen/ADP cartridge To determine the effect of the γ' chain peptide on the enzymatic activity of thrombin, the following assays may be performed.

Fibrinopeptide Cleavage Assay. Thrombin activity towards γA/γA and γA/γ fibrinogen may be measured by the rate of release of fibrinopeptides A and B. The reactions may be performed in 0.15 M NaCl/1 mM $CaCl_2$/20 mM HEPES, pH 7.4 at room temperature in the presence of 0-1 mM γ' peptide or scrambled peptide. The final concentrations of thrombin and fibrinogen may be 0.01 units/ml (0.10 nM) and 0.085 mg/ml (250 nM), respectively. Fibrinopeptide release may be monitored by reverse phase HPLC, since fibrinopeptides are difficult to resolve accurately using SDS-PAGE and each fibrinopeptide may be quantitated from the peak area (Lord et al., 1996). The rate constants may be calculated as described by Lord et al. (1996).

Factor XI, Factor V, Factor VIII, Factor XIII, Protein C, and TAFI Cleavage Assays. Thrombin activity towards these protein substrates may be measured by the rate of cleavage of purified factor XI (Haematologic Technologies, Inc.), factor V (Haematologic Technologies, Inc.), factor VIII (American Diagnostica), factor XIII (Enzyme Research), protein C (Haematologic Technologies, Inc.), and TAFI (Haematologic Technologies, Inc.), as monitored by SDS-PAGE (Laemmli, 1970). The reactions may be performed in 0.15 M NaCl/1 mM $CaCl_2$/20 mM HEPES, pH 7.4 at room temperature in the presence of 0-1 mM γ' peptide or scrambled peptide. The final concentrations of thrombin and substrates may be 0.01 units/ml (0.11 nM) and 250 nM, respectively. The cleavage reactions may be terminated by the addition of SDS-PAGE sample buffer. Samples are separable by SDS-PAGE and may be visualized by staining with Coomassie Brilliant Blue R-250. Gels may be scanned using a ChemiImager 4000 (Alpha Innotec Corp.), and the band intensity quantitated using NIH Image 1.62 software. Serial dilutions of each sample may be stained to ensure that the measured band intensities are within the linear range of staining.

The following protocols may be used to determine the effect of a γ' chain peptide in rat models of thrombosis. Pharmacokinetics of the γ' Peptide. The half-life of the γ' peptide in the rat circulatory system may be measured in order to establish a therapeutic dose of a γ' peptide for use in a rat model of thrombosis. The γ' peptide may be labeled with $^{125}$I-Bolton-Hunter reagent (Bolton & Hunter, 1973) at the amino terminus according to the manufacturer's protocol (Amersham). (A free amino terminus is not required for the anticoagulant activity of the γ' peptide.) 5 μg of γ' peptide in 10 μl 0.1 M borate, pH 8.5 may be added to dried $^{125}$I-Bolton-Hunter reagent for 15 minutes on ice and then quenched with 190 μl 0.2 M glycine/0.1 M borate pH 8.5. The labeled peptide may be desalted on Sephadex G-15 in 0.15 M NaCl/1 mM $CaCl_2$/20 mM HEPES, pH 7.4/1 mg/ml bovine serum albumin. $^{125}$I-labeled γ' peptide may be injected intravenously (i.v.) into three rats, and 100 μl blood samples taken every 10-15 minutes for 2 hours and counted in a gamma counter. From these data, the half-life of the peptide may be calculated. A bolus dose that maintains a circulating level of γ' peptide sufficient to double the aPTT at the end of the 60 minute thrombosis assays may be used as the highest dose for the thrombosis models described hereinbelow.

Rat Model of Arterial Thrombosis. The ferric chloride (FeCl$_3$) injury model developed by Kurz et al. (1990, Thromb Res 60:269-280), as modified by Konstantinides et al. (2001, Circulation 103: 576-583), may be used to assess arterial thrombosis. In this model, a FeCl$_3$ solution may be applied to an exposed carotid artery, and the time to occlusion measured with an ultrasonic probe. Other models of acute thrombosis in rodents, including electrical damage (Carmeliet et al. 1997), crush injury (Chen et al., 1996), and suture implantation (Tonken et al., 1995), may also be used to advantage to evaluate the effects of γ' peptide in vivo. The ferric chloride model is an exemplary in vivo assay system because it is simple, reproducible, and is in widespread use. In this model, platelet-rich clots containing fibrin and erythrocytes are formed, which are sensitive to heparin inhibition.

For such studies, 450-500 g Wistar rats may be anesthetized with Metofane and injected i.v. with either γ' peptides, heparin (500 IU/kg), or saline 30 minutes prior to the application of FeCl$_3$. Six rats may be used for each group, and each experiment performed three times to provide sufficient statistical power to measure differences between groups. The left carotid artery may be dissected and a 0.5×1.0 mm strip of Whatman No. 1 filter paper soaked in 35% FeCl$_3$ solution applied to the surface of the adventitia for three minutes. In previous studies, this has led to complete occlusion by 60 minutes in 96% of the animals (Kurz et al., 1990, Thromb Res 60: 269-280). Carotid blood flow may be monitored with a miniature ultrasound flow probe (0.5VB, Transonic Systems) interfaced with a flowmeter (model T106, Transonic Systems) and a computerized data acquisition program (WinDaq, DATAQ Instruments). At the end of a 60 minute flow-monitoring period, the rats may be killed with an overdose of anesthetic. Vascular patency rates vs. time may be examined by $\chi^2$ and Fisher's exact test. The results from such studies may be used to quantitate the antithrombotic activity of the γ' peptides in terms of their effect on 1) flow velocity with time, and 2) time to occlusion.

Rat Model of Venous Thrombosis. The shunt thrombosis model of Peters et al. (1991) may be used to assess venous thrombosis. In this model, a cotton thread may be inserted into the vena cava, and the resulting thrombus removed and analyzed. This model results in the development of fibrin-rich clots. It provides a very sensitive assay for heparin inhibition, and as a consequence may be more sensitive to the γ' heparin-like peptide.

450-500 g Wistar rats may be anesthetized with Metofane and injected i.v. with either γ' peptides, heparin (500 IU/kg), or saline 30 minutes prior to insertion of the cotton string. Six rats may be used for each group, and each experiment performed three times as described above. The jugular vein and contralateral carotid artery may be exposed and cannulated with polyethylene tubing. The saline-filled shunt assembly may be connected between the two cannulae and blood allowed to flow through it. The shunt assembly may consist of two lengths of polyethylene tubing connected by polyvinyl chloride tubing containing a length (5 cm) of cotton thread (Atlas white cotton thread 50, J and P Coats, Paisley, UK). A polyvinyl chloride plug (8 mm length) may be used to provide a connection at the inflow (arterial) end and to secure the thread. A siliconized polypropylene tapered connector (Gilson yellow pipette tip C20) bent to an angle of approximately 120° using a hot-air blower and shortened by 1 cm at the tip may be used to secure the outflow (venous) end.

After 15 minutes of blood flow, the shunt may be removed, and, after careful rinsing with trisodium citrate (5 ml, 5% w/v), the thread and associated thrombus may be cut at the inner ends of the inflow and outflow connectors, withdrawn, placed in a vial and weighed. The weight of thrombus formed on the thread may be calculated by deducting the average wet weight of an equivalent length (4 cm) of thread. Statistical analysis of the results may be performed using a Student's t-test. The results from these studies provide quantitation of the antithrombotic activity of the γ' peptides in terms of their effect on thrombus mass.

Results

Figure 12:
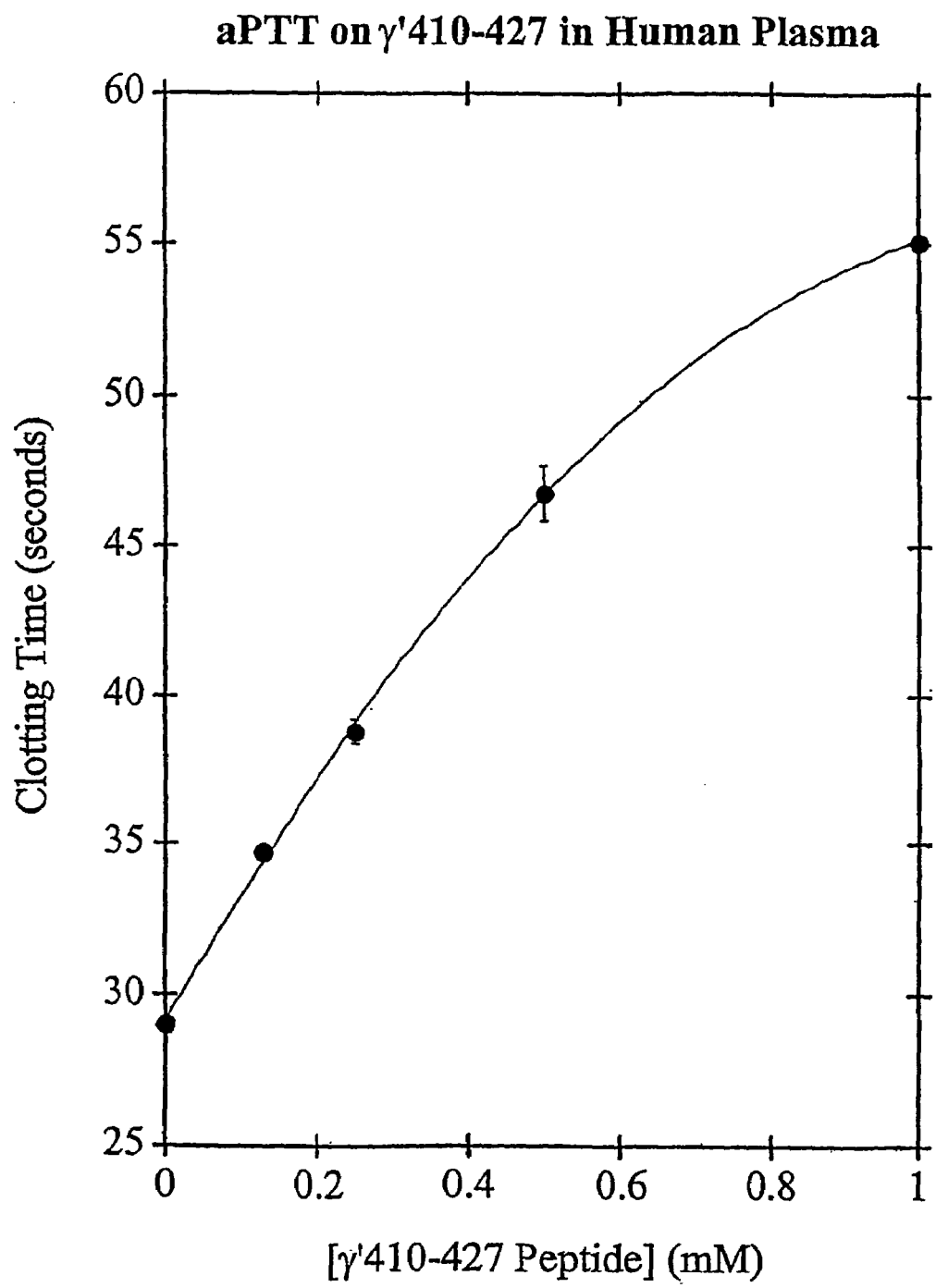
FIG. 12 shows a graph of the clotting time as a function of γ' 410-427 peptide concentration in an activated partial thromboplastin time (aPTT) assay in human plasma.

An aPTT assay was performed using human plasma to determine the effect of γ' peptide on the clotting time in this system. In brief, 0-1 mM γ' peptide was added to 50 μl of normal human reference plasma (Ortho) and manually loaded into an MLA 1600 (Organon Teknika). The MLA 1600 added SynthASil aPTT (Ortho) to initiate clotting and clot formation was monitored spectrophotometrically for 106 seconds. The data from this analysis are depicted graphically in FIG. 12. The results of these aPTT assays demonstrated that the γ' peptide exhibited an anticoagulant effect in human plasma.

Figure 13:
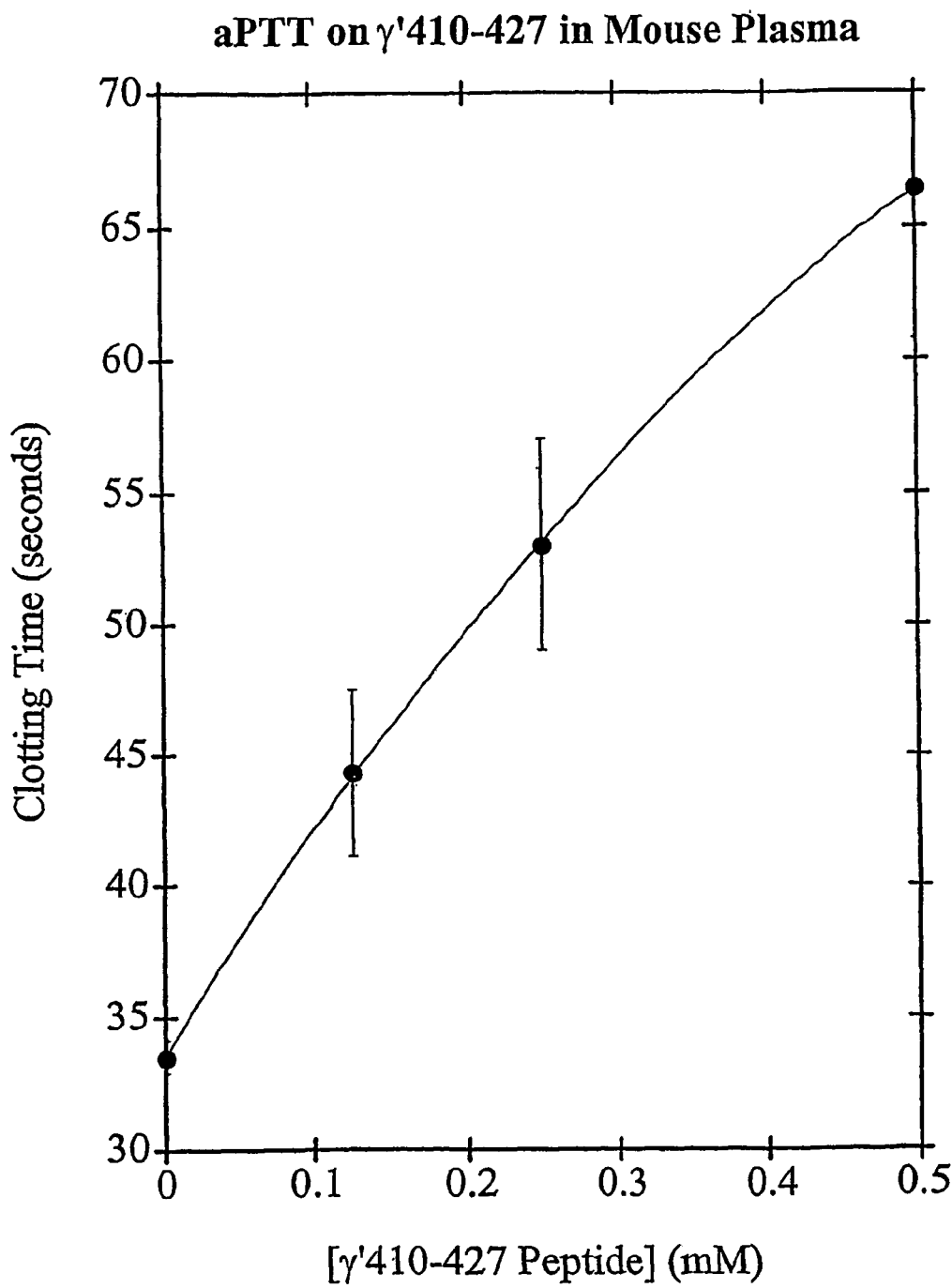
FIG. 13 shows a graph of the clotting time as a function of γ' 410-427 peptide concentration in an aPTT assay in mouse plasma.

An aPTT assay was performed using mouse plasma to determine the effect of γ' peptide on the clotting time in this system. In brief, 0-1 mM γ' peptide was added to 50 μl of normal mouse reference plasma (Ortho) and manually loaded into an MLA 1600 (Organon Teknika). The MLA 1600 added SynthASil aPTT reagent (Ortho) to initiate clotting and clot formation was monitored spectrophotometrically for 106 seconds. The results of this analysis demonstrated the anticoagulant effect of the γ' peptide on an aPTT assay performed with mouse plasma. See FIG. 13.

Figure 14:
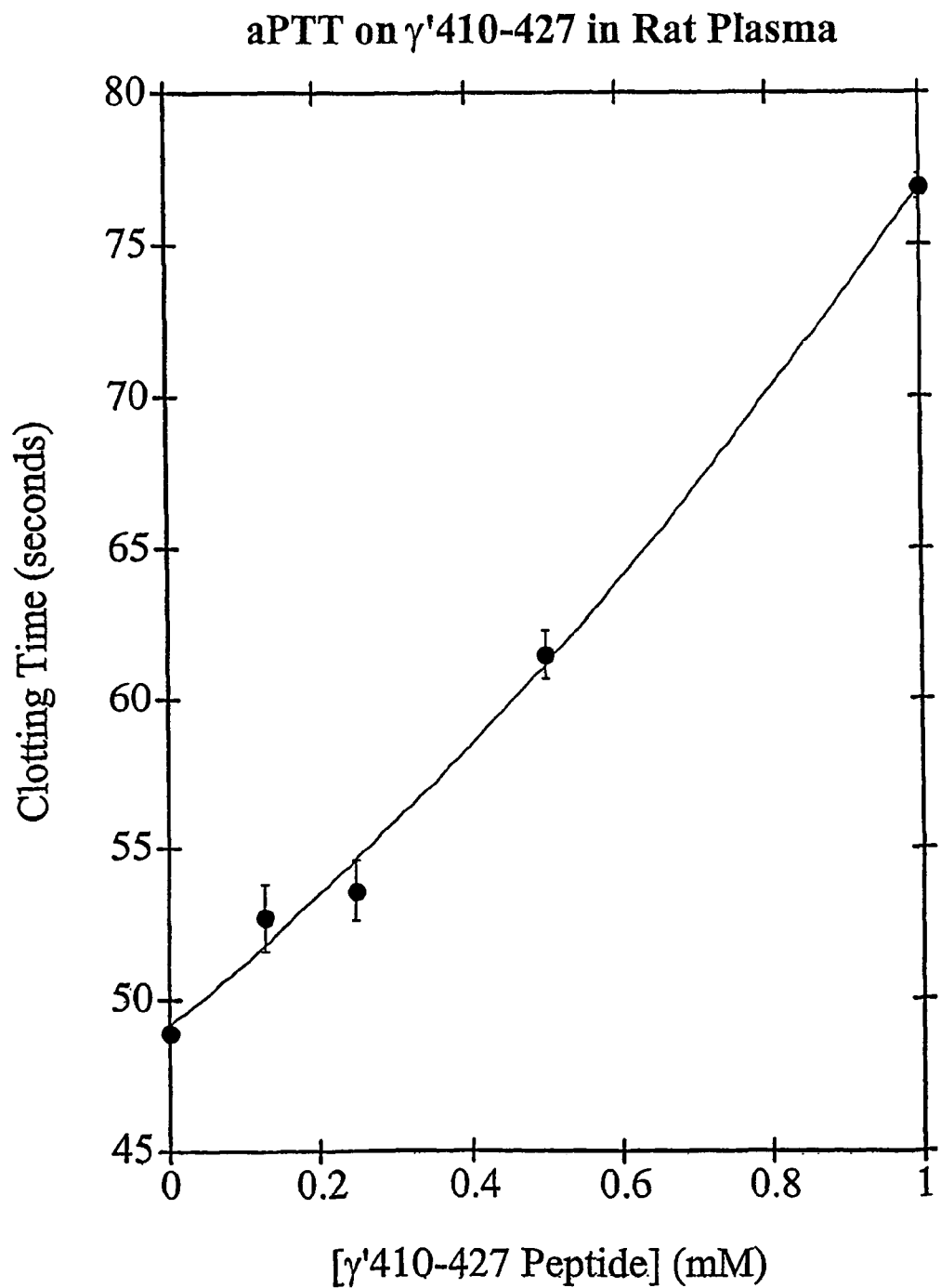
FIG. 14 shows a graph of the clotting time as a function of γ' 410-427 peptide concentration in an aPTT assay in rat plasma.

An aPTT assay was performed using rat plasma to determine the effect of γ' peptide on the clotting time in this system. In brief, 0-1 mM γ' peptide was added to 50 μl of normal rat reference plasma (Ortho) and manually loaded into an MLA 1600 (Organon Teknika). The MLA 1600 added SynthASil aPTT reagent (Ortho) to initiate clotting and clot formation was monitored spectrophotometrically for 106 seconds. The results of this analysis revealed that the γ' peptide exhibited anticoagulant properties in rat plasma. See FIG. 14.

Figure 15:
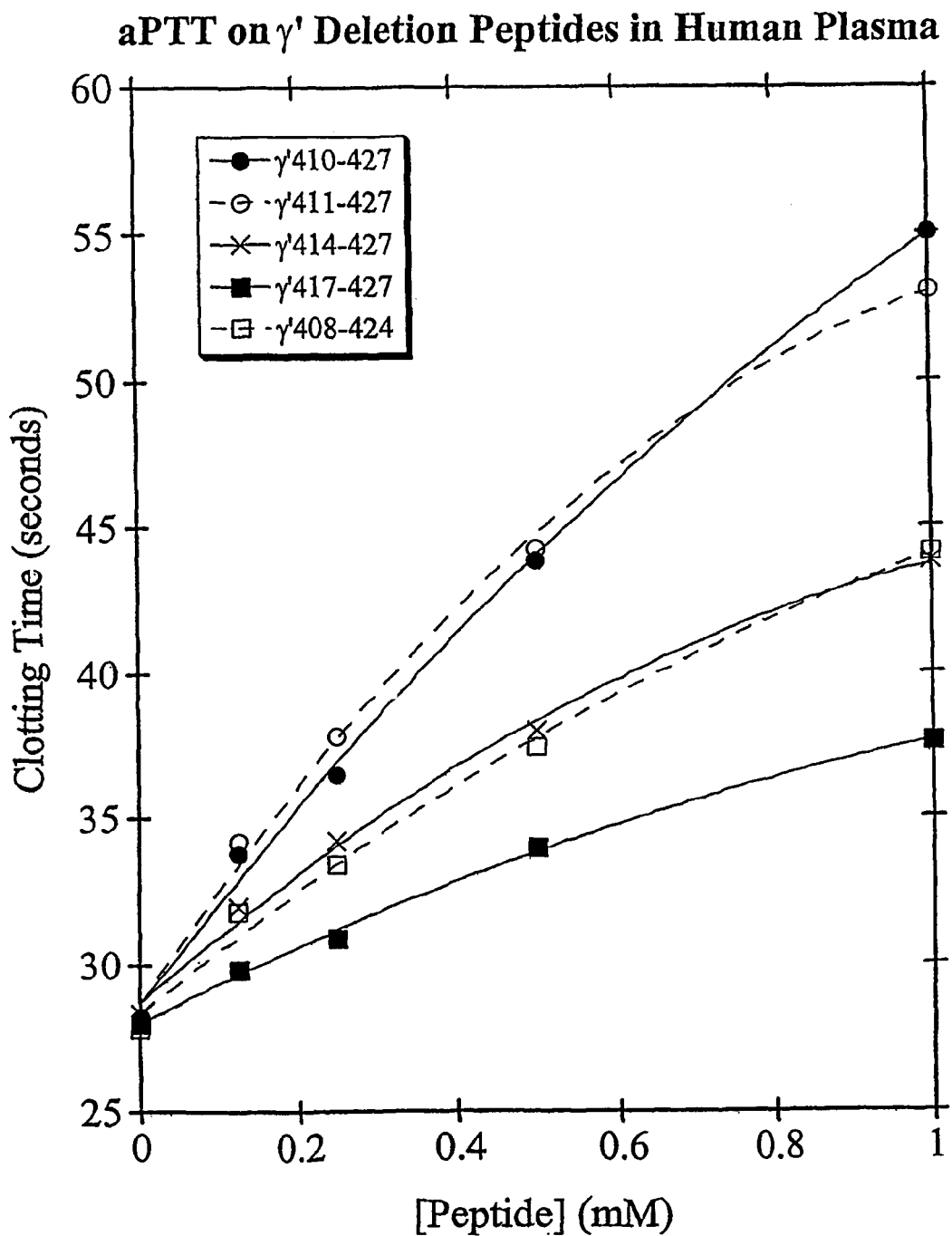
FIG. 15 shows a graph of the clotting time as a function of the concentration of different γ' deletion peptides in an aPTT assay in human plasma.

An aPTT assay was performed using human plasma to determine the effect of γ' deletion peptides on the clotting time in this system. See FIG. 15. The indicated γ' deletion peptides (0-1 mM) were added to 50 μl of normal human reference plasma (Ortho) and manually loaded into an MLA 1600 (Organon Teknika). The MLA 1600 added SynthASil aPTT reagent (Ortho) to initiate clotting and clot formation was monitored spectrophotometrically for 106 seconds. The differential anticoagulant effects of the various γ' deletion peptides in this assay revealed that different regions of the γ' peptide were critical for the activity of the full length peptide. The reduced level of anticoagulant activity associated with the 414-427 deletion peptide suggested that the string of Glu-His-Pro residues deleted therefrom made a substantial contribution to the activity of the full length peptide. The further reduction in activity observed with the 417-427 deletion peptide suggested that the three residues (Ala-Glu-Thr) deleted from this truncated peptide also made a substantial contribution to the activity of the full length peptide. The activity of the 408-424 deletion mutant, which was missing the three carboxy terminal residues (Asp-Asp-Leu), implicated this string of negatively charged amino acids as important for the activity of the full length γ' peptide. The data presented herein suggest that the negatively charged amino acid residues of the γ' peptide may be important for the stability and/or binding of the peptide, as reflected in the abrogated anticoagulant activity of derivatives from which such residues have been deleted.

Platelet aggregation assays were performed as described hereinabove. A PAP-4 platelet aggregometer (Bio/Data) was used to quantitate the effect of the γ' peptide on platelet aggregation, using the manufacturer's protocol. Based on the results presented hereinabove, it was anticipated that platelet aggregation in platelet-rich plasma would be strongly inhibited in the presence of γ' peptide when the platelet agonist was thrombin, but would not be inhibited as strongly when the platelet agonist was ADP, arachidonic acid, or epinephrine.

Normal platelet-rich plasma was generated by centrifugation of whole blood collected in 1/10 volume 0.294% sodium citrate/0.210% citric acid. Blood was centrifuged for 10 minutes at 1,000×g, and the supernatant of platelet-rich plasma was separated. 0-1 mM γ' peptide was added to 450 μl of platelet-rich plasma and loaded into siliconized cuvettes. 50 μl of agonist was added, and the absorbance was monitored for 6 minutes. The agonists used were 2 μM ADP (Sigma), 0.5 mg/ml arachidonic acid (Bio/Data), 10 μg/ml epinephrine (American Reagent Laboratories), or 0.2 units/ml thrombin. The results of this analysis demonstrated the anti-platelet effect of the γ' peptide on platelet aggregation, especially thrombin-induced aggregation. See Table 3.

| [γ'410-427] (mM) | ADP | | Arachidonic Acid | | Epinephrine | | Thrombin | |
|---|---|---|---|---|---|---|---|---|
| | Slope | Extent | Slope | Extent | Slope | Extent | Slope | Extent |
| 0 | 47 | 83% | 32 | 82% | 24 | 83% | 113 | 97% |
| 0.125 | 43 | 87% | 33 | 81% | 22 | 84% | 70 | 68% |
| 0.25 | 40 | 86% | 35 | 82% | 20 | 82% | 39 | 64% |
| 0.5 | 39 | 82% | 31 | 83% | 16 | 78% | 21 | 93% |
| 1.0 | 32 | 58% | 34 | 85% | 9 | 43% | 10 | 33% |

EXAMPLE IV

Diphosphorylated/Disulfated Synthetic Deletion Peptide Analogs Having Anti-Coagulant Activity Table 4 provides a list of exemplary γ' deletion peptides which may be used to advantage as anticoagulant agents. The "Y(*)" stands for phosphotyrosine (PO₃) (e.g., acid-stable phosphotyrosine) or sulfotyrosine (SO₃).

TABLE IV

| Amino Acid Sequence | Amino Acid Position | SEQ ID NO: |
|---|---|---|
| VRPEHPAETEY(*)DSLY(*)PE | 408-424 | 17 |
| PEHPAETEY(*)DSLY(*)PEDDL | 410-427 | 18 |
| EHPAETEY(*)DSLY(*)PEDDL | 411-427 | 19 |
| HPAETEY(*)DSLY(*)PEDDL | 412-427 | 20 |
| PAETEY(*)DSLY(*)PEDDL | 413-427 | 21 |
| AETEY(*)DSLY(*)PEDDL | 414-427 | 22 |
| ETEY(*)DSLY(*)PEDDL | 415-427 | 23 |
| TEY(*)DSLY(*)PEDDL | 416-427 | 24 |
| EY(*)DSLY(*)PEDDL | 417-427 | 25 |
| Y(*)DSLY(*)PEDDL | 418-427 | 26 |
| DSLY(*)PEDDL | 419-427 | 27 |
| SLY(*)PEDDL | 420-427 | 28 |
| Y(*)PEDDL | 421-427 | 29 |

TABLE IV-continued

| Amino Acid Sequence | Amino Acid Position | SEQ ID NO: |
|---|---|---|
| PEHPAETEY(*)DSLY(*)PEDD | 410-426 | 30 |
| PEHPAETEY(*)DSLY(*)PED | 410-425 | 31 |
| PEHPAETEY(*)DSLY(*)PE | 410-424 | 32 |
| PEHPAETEY(*)DSLY(*)P | 410-423 | 33 |
| PEHPAETEY(*)DSLY(*) | 410-422 | 34 |
| PEHPAETEY(*)DSL | 410-421 | 35 |
| PEHPAETEY(*)DS | 410-420 | 36 |
| PEHPAETEY(*)D | 410-419 | 37 |
| PEHPAETEY(*) | 410-418 | 38 |
| EHPAETEY(*)DSLY(*)PEDD | 411-426 | 39 |
| HPAETEY(*)DSLY(*)PEDD | 412-426 | 40 |
| PAETEY(*)DSLY(*)PEDD | 413-426 | 41 |
| AETEY(*)DSLY(*)PEDD | 414-426 | 42 |
| ETEY(*)DSLY(*)PEDD | 415-426 | 43 |
| TEY(*)DSLY(*)PEDD | 416-426 | 44 |
| EY(*)DSLY(*)PEDD | 417-426 | 45 |
| AETEY(*)DSLY(*)PED | 414-425 | 46 |
| AETEY(*)DSLY(*)PE | 414-424 | 47 |
| PEHPAETEY(*) | 410-418 | 48 |
| DSLY(*)PEDDL | 419-427 | 49 |
| DDEPY(*)LSDY(*)ETEA | 426-414 | 50 |
| LDDEPY(*)LSDY(*)ETEA | 427-414 | 51 |

The diphosphorylated/disulfated peptides listed in Table 4 may be further modified to include the substitutions γ' T416V and γ' S420V, either alone or in combination. Conservative amino acid substitutions at positions throughout the diphosphorylated/disulfated γ' peptides listed in Table 4, such as those provided in Table 2, are also encompassed by the present invention.

Additional γ' deletion peptides may be generated to identify residues which are important or critical for γ' peptide activity.

Synthetic peptides corresponding to the carboxyl terminus of the γ' chain may be synthesized with alanine-scanning mutations to identify individual residues that are important for the anticoagulant activity. In this approach, an alanine residue may be substituted for each of the charged amino acids in the γ' extension. This approach provides information about the role of individual residues in the activity, whereas the deletion approach provides information about the minimum chain length required for activity. The rationale for this approach is that the single alanine substitution is less likely to disrupt the tertiary structure of a peptide than deletions or other substitutions. Each peptide so generated may be tested in the aPTT assay, for example, described above for anticoagulant activity. Such methods may be used to delineate individual residues that are important for γ' peptide anticoagulant activity.

Such diphosphorylated/disulfated γ' peptides may be synthesized or generated by recombinant means as described hereinabove and by standard methods known in the art.

REFERENCES

1. Blombäck, B. (1996) *Thromb. Res.* 83, 1-75.
2. Seegers, W. H., Nieft, M., and Loomis, E. C. (1945) *Science* 101, 520-521.
3. Meh, D. A., Siebenlist, K. R., and Mosesson, M. W. (1996) *J. Biol. Chem.* 271, 23121-23125.
4. Kaczmarek, E., and McDonagh, J. (1988) *J. Biol. Chem.* 263, 13896-13900.
5. van Nispen, J. W., Hageman, T. C., and Scheraga, H. A. (1977) *Arch. Biochem. Biophys.* 182, 227-243.

6. Meh, D. A., Siebenlist, K. R., Brennan, S. O., Holyst, T., and Mosesson, M. W. (2001) *Thromb. Haemost.* 85, 470-474.
7. Chung, D. W., and Davie, E. W. (1984) *Biochemistry* 23, 4232-4236.
8. Fornace, A. J., Jr., Cummings, D., Comeau, C. M., Kant, J. A., and Crabtree, G. R. (1984) *J. Biol. Chem.* 259, 12826-12830.
9. Mosesson, M. W., and Finlayson, J. S. (1963) *J. Clin. Invest.* 42, 747-755.
10. Farrell, D. H., Mulvihill, E. R., Huang, S., Chung, D. W., and Davie, E. W. (1991) *Biochemistry* 30, 9414-9420.
11. Francis, C. W., Marder, V. J., and Martin, S. E. (1980) *J. Biol. Chem.* 255, 5599-5604.
12. Wolfenstein-Todel, C., and Mosesson, M. W. (1980) *Proc. Natl. Acad. Sci. USA* 77, 5069-5073.
13. Haidaris, P. J., Peerschke, E. I. B., Marder, V. J., and Francis, C. W. (1989) *Blood* 74, 2437-2444.
14. Hogg, P. J., and Jackson, C. M. (1989) *Proc. Natl. Acad. Sci. USA* 86, 3619-3623.
15. Weitz, J. I., Hudoba, M., Massel, D., Maraganore, J., and Hirsh, J. (1990) *J. Clin. Invest.* 86, 385-391.
16. Rosenberg, R. D., and Damus, P. S. (1973) *J. Biol. Chem.* 248, 6490-6505.
17. Moaddel, M., Falls, L. A., and Farrell, D. H. (2000) *J. Biol. Chem.* 275, 32135-32140.
18. Falls, L. A., and Farrell, D. H. (1997) *J. Biol. Chem.* 272, 14251-14256.
19. Bode, W., Turk, D., and Karshikov, A. (1992) *Protein Sci.* 1, 426-471.
20. Fenton, J. W., II, Olson, T. A., Zabinski, M. P., and Wilner, G. D. (1988) *Biochemistry* 27, 7106-7112.
21. Myles, T., Church, F. C., Whinna, H. C., Monard, D., and Stone, S. R. (1998) *J. Biol. Chem.* 273, 31203-31208.
22. Mathews, I. I., Padmanabhan, K. P., Ganesh, V., Tulinsky, A., Ishii, M., Chen, J., Turck, C. W., Coughlin, S. R., and Fenton, J. W., II (1994) *Biochemistry* 33, 3266-3279.
23. Rydel, T. J., Ravichandran, K. G., Tulinsky, A., Bode, W., Huber, R., Roitsch, C., and Fenton, J. W., II (1990) *Science* 249, 277-280.
24. Stubbs, M. T., and Bode, W. (1993) *Thromb. Res.* 69, 1-58.
25. Tulinsky, A., and Qiu, X. (1993) *Blood Coagul. Fibrinolysis* 4, 305-312.
26. Liu, L.-W., Rezaie, A. R., Carson, C. W., Esmon, N. L., and Esmon, C. T. (1994) *J. Biol. Chem.* 269, 11807-11812.
27. De Cristofaro, R., De Candia, E., Rutella, S., and Weitz, J. I. (2000) *J. Biol. Chem.* 275, 3887-3895.
28. Maraganore, J. M., Chao, B., Joseph, M. L., Jablonski, J., and Ramachandran, K. L. (1989) *J. Biol. Chem.* 264, 8692-8698.
29. Stone, S. R., and Hofsteenge, J. (1986) *Biochemistry* 25, 4622-4628.
30. Hortin, G. L., Tollefsen, D. M., and Strauss, A. W. (1986) *J. Biol. Chem.* 261, 15827-15830.
31. Marchese, P., Murata, M., Mazzucato, M., Pradella, P., De Marco, L., Ware, J., and Ruggeri, Z. M. (1995) *J. Biol. Chem.* 270, 9571-9578.
32. Pittman, D. D., Tomkinson, K. N., Michnick, D., Selighsohn, U., and Kaufman, R. J. (1994) *Biochemistry* 33, 6952-6959.
33. Michnick, D. A., Pittman, D. D., Wise, R. J., and Kaufman, R. J. (1994) *J. Biol. Chem.* 269, 20095-20102.
34. Colwell, N. S., Blinder, M. A., Tsiang, M., Gibbs, C. S., Bock, P. E., and Tollefsen, D. M. (1998) *Biochemistry* 37, 15057-15065.
35. Kunkel, T. A. (1985) *Proc. Natl. Acad. Sci USA* 82, 488-492.
36. Laemmli, U. K. (1970) *Nature* 227, 680-685.
37. Brown, W. M., Dziegielewska, K. M., Foreman, R. C., and Saunders, N. R. (1989) *Nucleic Acids Res.* 17, 6397.
38. Crabtree, G. R., and Kant, J. A. (1982) *Cell* 31, 159-166.
39. Hirose, S., Oda, K., and Ikehara, Y. (1988) *J. Biol. Chem.* 263, 7426-7430.
40. Lin, W. H., Larsen, K., Hortin, G. L., and Roth, J. A. (1992) *J. Biol. Chem.* 267, 2876-2879.
41. Henschen, A. (1993) *Blood Coag. Fibrinolysis* 4, 822.
42. Witting, J. I., Bourdon, P., Brezniak, D. V., Maraganore, J. M., and Fenton, J. W., II (1992) *Biochem. J.* 283, 737-743.
43. Hortin, G. L., and Benutto, B. M. (1990) *Biochem. Biophys. Res. Commun.* 169, 437-442.
44. Kaminski, M., and McDonagh, J. (1987) *Biochem. J.* 242, 881-887.
45. Hogg, P. J., Jackson, C. M., Labanowski, J. K., and Bock, P. E. (1996) *J. Biol. Chem.* 271, 26088-26095.
46. Becker, D. L., Fredenburgh, J. C., Stafford, A. R., and Weitz, J. I. (1999) *J. Biol. Chem.* 274, 6226-6233.
47. Zhao and Sane. (1993) *Arch Biochem Biophys* 304, 434-42.
48. Lovely, R. S., Moaddel, M., and Farrell, D. H. (2002) In press, *J. Thromb. Haemost.*
49. Lovely, R. S., Falls, L. A., Al-Mondhiry, H. A., Chambers, C. E., Sexton, G. J., Ni, H., and Farrell, D. H. (2002) In press, *Thromb. Haemost.*

Boston, A. E. & Hunter, W. M. (1973) *Biochem. J.* 133:529-539.
Carmeliet, P., et al. (1997) *Am. J. Pathol.* 150: 76-776.
Chen, L. E., et al. (1996) *J. Reconstr Microsurg* 12:31-38.
Lord, S. T., et al. (1996) *Biochemistry* 35:2342-2348.
Peters, R. F. (1991) *Thromb. Haemost.* 65:268-274.
Tonken, H. P., et al. (1995) *Microsurgery* 16: 98-102.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A peptide having anti-coagulation activity consisting of the amino acid sequence of SEQ ID NO: 56, wherein the tyrosine residues of the peptide are modified by phosphorylation or sulfation to increase the anti-coagulation activity of the cleaved peptide, wherein at least one of said tyrosine residues is modified by phosphorylation.

2. The peptide as claimed in claim 1 wherein both of said tyrosine residues are phosphorylated.

3. The peptide as claimed in claim 1 wherein one of said tyrosine residues is phosphorylated and one is sulfated.

4. A composition comprising the peptide of claim 1, in a pharmaceutically acceptable carrier.

5. A composition comprising the peptide of claim 2, in a pharmaceutically acceptable carrier.

6. A composition comprising the peptide of claim 3, in a pharmaceutically acceptable carrier.

7. An anti-coagulation peptide selected from the group consisting of SEQ ID NOs: 17-47, wherein tyrosine residues are modified by phosphorylation or sulfation to increase the anti-coagulation activity of the peptide.

8. The anti-coagulation peptide as claimed in claim 7 wherein at least one of said tyrosine residues is modified by phosphorylation.

9. The anti-coagulation peptide as claimed in claim 7 wherein at least one of said tyrosine residues is modified by sulfation.

10. The anti-coagulation peptide as claimed in claim 7 wherein one of said tyrosine residues is modified by phosphorylation and one of said tyrosine residues is modified by sulfation.

11. The anti-coagulation peptide as claimed in claim 8, wherein said anti-coagulation peptide further comprises at least one amino acid substitution selected from the group consisting of a valine substituted for a threonine and a valine substituted for a serine.

12. The anti-coagulation peptide as claimed in claim 9, wherein said anti-coagulation peptide further comprises at least one amino acid substitution selected from the group consisting of a valine substituted for a threonine and a valine substituted for a serine.

13. The anti-coagulation peptide as claimed in claim 10, wherein said anti-coagulation peptide further comprises at least one amino acid substitution selected from the group consisting of a valine substituted for a threonine and a valine substituted for a serine.

14. A composition comprising at least one of said anti-coagulation peptides of claim 7, in a pharmaceutically acceptable carrier.

15. A composition comprising at least one of said anti-coagulation peptides of claim 8, in a pharmaceutically acceptable carrier.

16. A composition comprising at least one of said anti-coagulation peptides of claim 9, in a pharmaceutically acceptable carrier.

17. A composition comprising at least one of said anti-coagulation peptides of claim 10, in a pharmaceutically acceptable carrier.

18. A composition comprising at least one of said anti-coagulation peptides of claim 11, in a pharmaceutically acceptable carrier.

19. A composition comprising at least one of said anti-coagulation peptides of claim 12, in a pharmaceutically acceptable carrier.

20. A composition comprising at least one of said anti-coagulation peptides of claim 13, in a pharmaceutically acceptable carrier.

21. A synthetic anti-coagulation peptide selected from the group consisting of SEQ ID NOs: 17-47, wherein the tyrosine residues are modified by phosphorylation or sulfation, and wherein the peptide comprises at least one amino acid substitution selected from the group consisting of a valine substituted for a threonine, a valine substituted for a serine, and conservative amino acid substitution, wherein said conservative amino acid substitution is the replacement of an amino acid for another amino acid in the same group of amino acids as defined in Table II.

22. A composition comprising at least one of said synthetic anti-coagulation peptides of claim 21, in a pharmaceutically acceptable carrier.

23. A synthetic anti-coagulation peptide of claim 21, wherein said peptide is modified by acylation.

24. A synthetic anti-coagulation peptide of claim 23, wherein said acylation modification comprises acetylation at the amino terminus.

25. The anti-coagulation peptide of claim 7 selected from the group consisting of SEQ ID NOs: 17, 19 and 22, wherein tyrosine residues are modified by phosphorylation or sulfation to increase the anti-coagulation activity of the peptide.

26. The anti-coagulation peptide as claimed in claim 25 wherein at least one of said tyrosine residues is modified by phosphorylation.

27. The anti-coagulation peptide as claimed in claim 25 wherein at least one of said tyrosine residues is modified by sulfation.

28. The anti-coagulation peptide as claimed in claim 25 wherein one of said tyrosine residues is modified by phosphorylation and one of said tyrosine residues is modified by sulfation.

29. The anti-coagulation peptide of claim 1, wherein said peptide is modified by acylation.

30. The anti-coagulation peptide of claim 29, wherein said acylation modification comprises acetylation at the amino terminus.

31. The anti-coagulation peptide of claim 7, wherein said peptide is modified by acylation.

32. The anti-coagulation peptide of claim 31, wherein said acylation modification comprises acetylation at the amino terminus.

33. The anti-coagulation peptide of claim 21, wherein said conservative amino acid substitution is selected from the group consisting of an isoleucine or leucine substituted for a valine, a lysine substituted for an arginine, an aspartic acid substituted for a glutamic acid, a glutamic acid substituted for an aspartic acid, a valine substituted for a threonine, an alanine substituted for a serine, and an isoleucine or valine substituted for an isoleucine.

* * * * *

SEQUENCE LISTING

<160> NUMBER OF SEQ ID NOS: 56

<210> SEQ ID NO 1
<211> LENGTH: 18
<212> TYPE: PRT
<213> ORGANISM: Homo Sapien

<400> SEQUENCE: 1

Pro Glu His Pro Ala Glu Thr Glu Tyr Asp Ser Leu Tyr Pro Glu Asp
1               5                   10                  15

Asp Leu

<210> SEQ ID NO 2
<211> LENGTH: 68
<212> TYPE: PRT
<213> ORGANISM: Homo Sapien

<400> SEQUENCE: 2

Met Ser Trp Ser Leu His Pro Arg Asn Leu Ile Leu Tyr Phe Tyr Ala
1               5                   10                  15

Leu Leu Phe Leu Ser Ser Thr Cys Val Ala His His His His His His
                20                  25                  30

Ala Ala Ala Ala Ala Ala Ala Ala Ala Ala Ala Ala Ala Ala
            35                  40                  45

Val Arg Pro Glu His Pro Ala Glu Thr Glu Tyr Asp Ser Leu Tyr Pro
        50                  55                  60

Glu Asp Asp Leu
65

<210> SEQ ID NO 3
<211> LENGTH: 46
<212> TYPE: PRT
<213> ORGANISM: Homo Sapien

<400> SEQUENCE: 3

Met Phe Ser Met Arg Ile Val Cys Leu Val Leu Ser Val Val Gly Thr
1               5                   10                  15

Ala Trp Thr Met Asp Tyr Lys Asp Asp Asp Lys Pro Glu His Pro
                20                  25                  30

Ala Glu Thr Glu Tyr Asp Ser Leu Tyr Pro Glu Asp Asp Leu
            35                  40                  45

<210> SEQ ID NO 4
<211> LENGTH: 51
<212> TYPE: PRT
<213> ORGANISM: Homo Sapien
<220> FEATURE:
<221> NAME/KEY: VARIANT
<222> LOCATION: 28, 29, 31
<223> OTHER INFORMATION: Xaa can be any amino acid

<400> SEQUENCE: 4

Met Lys His Leu Leu Leu Leu Leu Cys Val Phe Leu Val Lys Ser
1               5                   10                  15

Glu Gln Lys Leu Ile Ser Glu Glu Asp Leu Glu Xaa Xaa Tyr Xaa Gln
                20                  25                  30

Ser Pro Glu His Pro Ala Glu Thr Glu Tyr Asp Ser Leu Tyr Pro Glu
            35                  40                  45

Asp Asp Leu
    50

<210> SEQ ID NO 5
<211> LENGTH: 15
<212> TYPE: DNA
<213> ORGANISM: Artificial Sequence
<220> FEATURE:
<223> OTHER INFORMATION: primer

```
<400> SEQUENCE: 5
ggttggtgtg gttgg                                                        15

<210> SEQ ID NO 6
<211> LENGTH: 29
<212> TYPE: DNA
<213> ORGANISM: Artificial Sequence
<220> FEATURE:
<223> OTHER INFORMATION: primer

<400> SEQUENCE: 6
agtccgtggt agggcaggtt ggggtgact                                         29

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
gaaacagaat ttgactcact t                                                 21

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
gactcacttt tccctgagga t                                                 21

<210> SEQ ID NO 9
<211> LENGTH: 33
<212> TYPE: DNA
<213> ORGANISM: Artificial Sequence
<220> FEATURE:
<223> OTHER INFORMATION: primer

<400> SEQUENCE: 9
gaaacagaat ttgactcact tttccctgag gat                                    33

<210> SEQ ID NO 10
<211> LENGTH: 20
<212> TYPE: PRT
<213> ORGANISM: Homo Sapien
<220> FEATURE:
<221> NAME/KEY: MOD_RES
<222> LOCATION: 11, 15
<223> OTHER INFORMATION: Tyrosine is phosphotyrosine

<400> SEQUENCE: 10

Val Arg Pro Glu His Pro Ala Glu Thr Glu Tyr Asp Ser Leu Tyr Pro
 1               5                  10                  15

Glu Asp Asp Leu
            20

<210> SEQ ID NO 11
<211> LENGTH: 20
<212> TYPE: PRT
<213> ORGANISM: Homo Sapien

<400> SEQUENCE: 11

Val Arg Pro Glu His Pro Ala Glu Thr Glu Tyr Asp Ser Leu Tyr Pro
```

```
                1               5                  10                 15
Glu Asp Asp Leu
            20

<210> SEQ ID NO 12
<211> LENGTH: 7
<212> TYPE: PRT
<213> ORGANISM: Homo Sapien

<400> SEQUENCE: 12

Glu Glu Pro Glu Tyr Gly Glu
  1               5

<210> SEQ ID NO 13
<211> LENGTH: 9
<212> TYPE: PRT
<213> ORGANISM: Homo Sapien

<400> SEQUENCE: 13

Glu Glu Phe Glu Glu Ala Tyr Ile Pro
  1               5

<210> SEQ ID NO 14
<211> LENGTH: 68
<212> TYPE: PRT
<213> ORGANISM: Homo Sapien
<220> FEATURE:
<221> NAME/KEY: MOD_RES
<222> LOCATION: 59, 63
<223> OTHER INFORMATION: Tyrosine is sulfotyrosine

<400> SEQUENCE: 14

Met Ser Trp Ser Leu His Pro Arg Asn Leu Ile Leu Tyr Phe Tyr Ala
  1               5                  10                 15

Leu Leu Phe Leu Ser Ser Thr Cys Val Ala His His His His His His
                 20                  25                 30

Ala Ala Ala Ala Ala Ala Ala Ala Ala Ala Ala Ala Ala Ala Ala
            35                  40                 45

Val Arg Pro Glu His Pro Ala Glu Thr Glu Tyr Asp Ser Leu Tyr Pro
     50                  55                  60

Glu Asp Asp Leu
65

<210> SEQ ID NO 15
<211> LENGTH: 46
<212> TYPE: PRT
<213> ORGANISM: Homo Sapien
<220> FEATURE:
<221> NAME/KEY: MOD_RES
<222> LOCATION: 37, 41
<223> OTHER INFORMATION: Tyrosine is sulfotyrosine

<400> SEQUENCE: 15

Met Phe Ser Met Arg Ile Val Cys Leu Val Leu Ser Val Val Gly Thr
  1               5                  10                 15

Ala Trp Thr Met Asp Tyr Lys Asp Asp Asp Lys Pro Glu His Pro
                 20                  25                 30

Ala Glu Thr Glu Tyr Asp Ser Leu Tyr Pro Glu Asp Asp Leu
            35                  40                 45

<210> SEQ ID NO 16
<211> LENGTH: 51
<212> TYPE: PRT
```

```
<213> ORGANISM: Homo Sapien
<220> FEATURE:
<221> NAME/KEY: MOD_RES
<222> LOCATION: 42, 46
<223> OTHER INFORMATION: Tyrosine is sulfotyrosine
<220> FEATURE:
<221> NAME/KEY: VARIANT
<222> LOCATION: 28, 29, 31
<223> OTHER INFORMATION: Xaa can be any amino acid

<400> SEQUENCE: 16

Met Lys His Leu Leu Leu Leu Leu Cys Val Phe Leu Val Lys Ser
 1               5                  10                  15

Glu Gln Lys Leu Ile Ser Glu Glu Asp Leu Glu Xaa Xaa Tyr Xaa Gln
            20                  25                  30

Ser Pro Glu His Pro Ala Glu Thr Glu Tyr Asp Ser Leu Tyr Pro Glu
        35                  40                  45

Asp Asp Leu
    50

<210> SEQ ID NO 17
<211> LENGTH: 17
<212> TYPE: PRT
<213> ORGANISM: Homo Sapien
<220> FEATURE:
<221> NAME/KEY: PHOSPHORYLATION
<222> LOCATION: 11, 15
<223> OTHER INFORMATION: Tyrosine is phosphotyrosine or sulfotyrosine

<400> SEQUENCE: 17

Val Arg Pro Glu His Pro Ala Glu Thr Glu Tyr Asp Ser Leu Tyr Pro
 1               5                  10                  15

Glu

<210> SEQ ID NO 18
<211> LENGTH: 18
<212> TYPE: PRT
<213> ORGANISM: Homo Sapien
<220> FEATURE:
<221> NAME/KEY: PHOSPHORYLATION
<222> LOCATION: 9, 13
<223> OTHER INFORMATION: Tyrosine is phosphotyrosine or sulfotyrosine

<400> SEQUENCE: 18

Pro Glu His Pro Ala Glu Thr Glu Tyr Asp Ser Leu Tyr Pro Glu Asp
 1               5                  10                  15

Asp Leu

<210> SEQ ID NO 19
<211> LENGTH: 17
<212> TYPE: PRT
<213> ORGANISM: Homo Sapien
<220> FEATURE:
<221> NAME/KEY: PHOSPHORYLATION
<222> LOCATION: 8, 12
<223> OTHER INFORMATION: Tyrosine is phosphotyrosine or sulfotyrosine

<400> SEQUENCE: 19

Glu His Pro Ala Glu Thr Glu Tyr Asp Ser Leu Tyr Pro Glu Asp Asp
 1               5                  10                  15

Leu

<210> SEQ ID NO 20
<211> LENGTH: 16
<212> TYPE: PRT
```

```
<213> ORGANISM: Homo Sapien
<220> FEATURE:
<221> NAME/KEY: PHOSPHORYLATION
<222> LOCATION: 7, 11
<223> OTHER INFORMATION: Tyrosine is phosphotyrosine or sulfotyrosine

<400> SEQUENCE: 20

His Pro Ala Glu Thr Glu Tyr Asp Ser Leu Tyr Pro Glu Asp Asp Leu
1               5                   10                  15

<210> SEQ ID NO 21
<211> LENGTH: 15
<212> TYPE: PRT
<213> ORGANISM: Homo Sapien
<220> FEATURE:
<221> NAME/KEY: PHOSPHORYLATION
<222> LOCATION: 6, 10
<223> OTHER INFORMATION: Tyrosine is phosphotyrosine or sulfotyrosine

<400> SEQUENCE: 21

Pro Ala Glu Thr Glu Tyr Asp Ser Leu Tyr Pro Glu Asp Asp Leu
1               5                   10                  15

<210> SEQ ID NO 22
<211> LENGTH: 14
<212> TYPE: PRT
<213> ORGANISM: Homo Sapien
<220> FEATURE:
<221> NAME/KEY: PHOSPHORYLATION
<222> LOCATION: 5, 9
<223> OTHER INFORMATION: Tyrosine is phosphotyrosine or sulfotyrosine

<400> SEQUENCE: 22

Ala Glu Thr Glu Tyr Asp Ser Leu Tyr Pro Glu Asp Asp Leu
1               5                   10

<210> SEQ ID NO 23
<211> LENGTH: 13
<212> TYPE: PRT
<213> ORGANISM: Homo Sapien
<220> FEATURE:
<221> NAME/KEY: PHOSPHORYLATION
<222> LOCATION: 4, 8
<223> OTHER INFORMATION: Tyrosine is phosphotyrosine or sulfotyrosine

<400> SEQUENCE: 23

Glu Thr Glu Tyr Asp Ser Leu Tyr Pro Glu Asp Asp Leu
1               5                   10

<210> SEQ ID NO 24
<211> LENGTH: 12
<212> TYPE: PRT
<213> ORGANISM: Homo Sapien
<220> FEATURE:
<221> NAME/KEY: PHOSPHORYLATION
<222> LOCATION: 3, 7
<223> OTHER INFORMATION: Tyrosine is phosphotyrosine or sulfotyrosine

<400> SEQUENCE: 24

Thr Glu Tyr Asp Ser Leu Tyr Pro Glu Asp Asp Leu
1               5                   10

<210> SEQ ID NO 25
<211> LENGTH: 11
<212> TYPE: PRT
<213> ORGANISM: Homo Sapien
<220> FEATURE:
<221> NAME/KEY: PHOSPHORYLATION
<222> LOCATION: 2, 6
```

<223> OTHER INFORMATION: Tyrosine is phosphotyrosine or sulfotyrosine

<400> SEQUENCE: 25

Glu Tyr Asp Ser Leu Tyr Pro Glu Asp Asp Leu
1               5                   10

<210> SEQ ID NO 26
<211> LENGTH: 10
<212> TYPE: PRT
<213> ORGANISM: Homo Sapien
<220> FEATURE:
<221> NAME/KEY: PHOSPHORYLATION
<222> LOCATION: 1, 5
<223> OTHER INFORMATION: Tyrosine is phosphotyrosine or sulfotyrosine

<400> SEQUENCE: 26

Tyr Asp Ser Leu Tyr Pro Glu Asp Asp Leu
1               5                   10

<210> SEQ ID NO 27
<211> LENGTH: 9
<212> TYPE: PRT
<213> ORGANISM: Homo Sapien
<220> FEATURE:
<221> NAME/KEY: PHOSPHORYLATION
<222> LOCATION: 4
<223> OTHER INFORMATION: Tyrosine is phosphotyrosine or sulfotyrosine

<400> SEQUENCE: 27

Asp Ser Leu Tyr Pro Glu Asp Asp Leu
1               5

<210> SEQ ID NO 28
<211> LENGTH: 8
<212> TYPE: PRT
<213> ORGANISM: Homo Sapien
<220> FEATURE:
<221> NAME/KEY: PHOSPHORYLATION
<222> LOCATION: 3
<223> OTHER INFORMATION: Tyrosine is phosphotyrosine or sulfotyrosine

<400> SEQUENCE: 28

Ser Leu Tyr Pro Glu Asp Asp Leu
1               5

<210> SEQ ID NO 29
<211> LENGTH: 6
<212> TYPE: PRT
<213> ORGANISM: Homo Sapien
<220> FEATURE:
<221> NAME/KEY: PHOSPHORYLATION
<222> LOCATION: 1
<223> OTHER INFORMATION: Tyrosine is phosphotyrosine or sulfotyrosine

<400> SEQUENCE: 29

Tyr Pro Glu Asp Asp Leu
1               5

<210> SEQ ID NO 30
<211> LENGTH: 17
<212> TYPE: PRT
<213> ORGANISM: Homo Sapien
<220> FEATURE:
<221> NAME/KEY: PHOSPHORYLATION
<222> LOCATION: 9, 13
<223> OTHER INFORMATION: Tyrosine is phosphotyrosine or sulfotyrosine

<400> SEQUENCE: 30

-continued

Pro Glu His Pro Ala Glu Thr Glu Tyr Asp Ser Leu Tyr Pro Glu Asp
1               5                   10                  15

Asp

<210> SEQ ID NO 31
<211> LENGTH: 16
<212> TYPE: PRT
<213> ORGANISM: Homo Sapien
<220> FEATURE:
<221> NAME/KEY: PHOSPHORYLATION
<222> LOCATION: 9, 13
<223> OTHER INFORMATION: Tyrosine is phosphotyrosine or sulfotyrosine

<400> SEQUENCE: 31

Pro Glu His Pro Ala Glu Thr Glu Tyr Asp Ser Leu Tyr Pro Glu Asp
1               5                   10                  15

<210> SEQ ID NO 32
<211> LENGTH: 15
<212> TYPE: PRT
<213> ORGANISM: Homo Sapien
<220> FEATURE:
<221> NAME/KEY: PHOSPHORYLATION
<222> LOCATION: 9, 13
<223> OTHER INFORMATION: Tyrosine is phosphotyrosine or sulfotyrosine

<400> SEQUENCE: 32

Pro Glu His Pro Ala Glu Thr Glu Tyr Asp Ser Leu Tyr Pro Glu
1               5                   10                  15

<210> SEQ ID NO 33
<211> LENGTH: 14
<212> TYPE: PRT
<213> ORGANISM: Homo Sapien
<220> FEATURE:
<221> NAME/KEY: PHOSPHORYLATION
<222> LOCATION: 9, 13
<223> OTHER INFORMATION: Tyrosine is phosphotyrosine or sulfotyrosine

<400> SEQUENCE: 33

Pro Glu His Pro Ala Glu Thr Glu Tyr Asp Ser Leu Tyr Pro
1               5                   10

<210> SEQ ID NO 34
<211> LENGTH: 13
<212> TYPE: PRT
<213> ORGANISM: Homo Sapien
<220> FEATURE:
<221> NAME/KEY: PHOSPHORYLATION
<222> LOCATION: 9
<223> OTHER INFORMATION: Tyrosine is phosphotyrosine or sulfotyrosine

<400> SEQUENCE: 34

Pro Glu His Pro Ala Glu Thr Glu Tyr Asp Ser Leu Tyr
1               5                   10

<210> SEQ ID NO 35
<211> LENGTH: 12
<212> TYPE: PRT
<213> ORGANISM: Homo Sapien
<220> FEATURE:
<221> NAME/KEY: PHOSPHORYLATION
<222> LOCATION: 9
<223> OTHER INFORMATION: Tyrosine is phosphotyrosine or sulfotyrosine

<400> SEQUENCE: 35

Pro Glu His Pro Ala Glu Thr Glu Tyr Asp Ser Leu
1               5                   10

```
<210> SEQ ID NO 36
<211> LENGTH: 11
<212> TYPE: PRT
<213> ORGANISM: Homo Sapien
<220> FEATURE:
<221> NAME/KEY: PHOSPHORYLATION
<222> LOCATION: 9
<223> OTHER INFORMATION: Tyrosine is phosphotyrosine or sulfotyrosine

<400> SEQUENCE: 36

Pro Glu His Pro Ala Glu Thr Glu Tyr Asp Ser
 1               5                  10

<210> SEQ ID NO 37
<211> LENGTH: 10
<212> TYPE: PRT
<213> ORGANISM: Homo Sapien
<220> FEATURE:
<221> NAME/KEY: PHOSPHORYLATION
<222> LOCATION: 9
<223> OTHER INFORMATION: Tyrosine is phosphotyrosine or sulfotyrosine

<400> SEQUENCE: 37

Pro Glu His Pro Ala Glu Thr Glu Tyr Asp
 1               5                  10

<210> SEQ ID NO 38
<211> LENGTH: 9
<212> TYPE: PRT
<213> ORGANISM: Homo Sapien
<220> FEATURE:
<221> NAME/KEY: PHOSPHORYLATION
<222> LOCATION: 9
<223> OTHER INFORMATION: Tyrosine is phosphotyrosine or sulfotyrosine

<400> SEQUENCE: 38

Pro Glu His Pro Ala Glu Thr Glu Tyr
 1               5

<210> SEQ ID NO 39
<211> LENGTH: 16
<212> TYPE: PRT
<213> ORGANISM: Homo Sapien
<220> FEATURE:
<221> NAME/KEY: PHOSPHORYLATION
<222> LOCATION: 8, 12
<223> OTHER INFORMATION: Tyrosine is phosphotyrosine or sulfotyrosine

<400> SEQUENCE: 39

Glu His Pro Ala Glu Thr Glu Tyr Asp Ser Leu Tyr Pro Glu Asp Asp
 1               5                  10                  15

<210> SEQ ID NO 40
<211> LENGTH: 15
<212> TYPE: PRT
<213> ORGANISM: Homo Sapien
<220> FEATURE:
<221> NAME/KEY: PHOSPHORYLATION
<222> LOCATION: 7, 11
<223> OTHER INFORMATION: Tyrosine is phosphotyrosine or sulfotyrosine

<400> SEQUENCE: 40

His Pro Ala Glu Thr Glu Tyr Asp Ser Leu Tyr Pro Glu Asp Asp
 1               5                  10                  15

<210> SEQ ID NO 41
<211> LENGTH: 14
```

```
<212> TYPE: PRT
<213> ORGANISM: Homo Sapien
<220> FEATURE:
<221> NAME/KEY: PHOSPHORYLATION
<222> LOCATION: 6, 10
<223> OTHER INFORMATION: Tyrosine is phosphotyrosine or sulfotyrosine

<400> SEQUENCE: 41

Pro Ala Glu Thr Glu Tyr Asp Ser Leu Tyr Pro Glu Asp Asp
 1               5                  10

<210> SEQ ID NO 42
<211> LENGTH: 13
<212> TYPE: PRT
<213> ORGANISM: Homo Sapien
<220> FEATURE:
<221> NAME/KEY: PHOSPHORYLATION
<222> LOCATION: 5, 9
<223> OTHER INFORMATION: Tyrosine is phosphotyrosine or sulfotyrosine

<400> SEQUENCE: 42

Ala Glu Thr Glu Tyr Asp Ser Leu Tyr Pro Glu Asp Asp
 1               5                  10

<210> SEQ ID NO 43
<211> LENGTH: 12
<212> TYPE: PRT
<213> ORGANISM: Homo Sapien
<220> FEATURE:
<221> NAME/KEY: PHOSPHORYLATION
<222> LOCATION: 4, 8
<223> OTHER INFORMATION: Tyrosine is phosphotyrosine or sulfotyrosine

<400> SEQUENCE: 43

Glu Thr Glu Tyr Asp Ser Leu Tyr Pro Glu Asp Asp
 1               5                  10

<210> SEQ ID NO 44
<211> LENGTH: 11
<212> TYPE: PRT
<213> ORGANISM: Homo Sapien
<220> FEATURE:
<221> NAME/KEY: PHOSPHORYLATION
<222> LOCATION: 3, 7
<223> OTHER INFORMATION: Tyrosine is phosphotyrosine or sulfotyrosine

<400> SEQUENCE: 44

Thr Glu Tyr Asp Ser Leu Tyr Pro Glu Asp Asp
 1               5                  10

<210> SEQ ID NO 45
<211> LENGTH: 10
<212> TYPE: PRT
<213> ORGANISM: Homo Sapien
<220> FEATURE:
<221> NAME/KEY: PHOSPHORYLATION
<222> LOCATION: 2, 6
<223> OTHER INFORMATION: Tyrosine is phosphotyrosine or sulfotyrosine

<400> SEQUENCE: 45

Glu Tyr Asp Ser Leu Tyr Pro Glu Asp Asp
 1               5                  10

<210> SEQ ID NO 46
<211> LENGTH: 12
<212> TYPE: PRT
<213> ORGANISM: Homo Sapien
<220> FEATURE:
<221> NAME/KEY: PHOSPHORYLATION
```

-continued

```
<222> LOCATION: 5, 9
<223> OTHER INFORMATION: Tyrosine is phosphotyrosine or sulfotyrosine

<400> SEQUENCE: 46

Ala Glu Thr Glu Tyr Asp Ser Leu Tyr Pro Glu Asp
 1               5                  10

<210> SEQ ID NO 47
<211> LENGTH: 11
<212> TYPE: PRT
<213> ORGANISM: Homo Sapien
<220> FEATURE:
<221> NAME/KEY: PHOSPHORYLATION
<222> LOCATION: 5, 9
<223> OTHER INFORMATION: Tyrosine is phosphotyrosine or sulfotyrosine

<400> SEQUENCE: 47

Ala Glu Thr Glu Tyr Asp Ser Leu Tyr Pro Glu
 1               5                  10

<210> SEQ ID NO 48
<211> LENGTH: 9
<212> TYPE: PRT
<213> ORGANISM: Homo Sapien
<220> FEATURE:
<221> NAME/KEY: PHOSPHORYLATION
<222> LOCATION: 9
<223> OTHER INFORMATION: Tyrosine is phosphotyrosine or sulfotyrosine

<400> SEQUENCE: 48

Pro Glu His Pro Ala Glu Thr Glu Tyr
 1               5

<210> SEQ ID NO 49
<211> LENGTH: 9
<212> TYPE: PRT
<213> ORGANISM: Homo Sapien
<220> FEATURE:
<221> NAME/KEY: PHOSPHORYLATION
<222> LOCATION: 4
<223> OTHER INFORMATION: Tyrosine is phosphotyrosine or sulfotyrosine

<400> SEQUENCE: 49

Asp Ser Leu Tyr Pro Glu Asp Asp Leu
 1               5

<210> SEQ ID NO 50
<211> LENGTH: 13
<212> TYPE: PRT
<213> ORGANISM: Homo Sapien
<220> FEATURE:
<221> NAME/KEY: PHOSPHORYLATION
<222> LOCATION: 5, 9
<223> OTHER INFORMATION: Tyrosine is phosphotyrosine or sulfotyrosine

<400> SEQUENCE: 50

Asp Asp Glu Pro Tyr Leu Ser Asp Tyr Glu Thr Glu Ala
 1               5                  10

<210> SEQ ID NO 51
<211> LENGTH: 14
<212> TYPE: PRT
<213> ORGANISM: Homo Sapien
<220> FEATURE:
<221> NAME/KEY: PHOSPHORYLATION
<222> LOCATION: 6, 10
<223> OTHER INFORMATION: Tyrosine is phosphotyrosine or sulfotyrosine

<400> SEQUENCE: 51
```

Leu Asp Asp Glu Pro Tyr Leu Ser Asp Tyr Glu Thr Glu Ala
1               5                   10

<210> SEQ ID NO 52
<211> LENGTH: 4
<212> TYPE: PRT
<213> ORGANISM: Homo Sapien

<400> SEQUENCE: 52

Ala Gly Asp Val
1

<210> SEQ ID NO 53
<211> LENGTH: 20
<212> TYPE: PRT
<213> ORGANISM: Homo Sapien

<400> SEQUENCE: 53

Val Arg Pro Glu His Pro Ala Glu Thr Glu Phe Asp Ser Leu Tyr Pro
1               5                   10                  15

Glu Asp Asp Leu
            20

<210> SEQ ID NO 54
<211> LENGTH: 20
<212> TYPE: PRT
<213> ORGANISM: Homo Sapien

<400> SEQUENCE: 54

Val Arg Pro Glu His Pro Ala Glu Thr Glu Tyr Asp Ser Leu Phe Pro
1               5                   10                  15

Glu Asp Asp Leu
            20

<210> SEQ ID NO 55
<211> LENGTH: 20
<212> TYPE: PRT
<213> ORGANISM: Homo Sapien

<400> SEQUENCE: 55

Val Arg Pro Glu His Pro Ala Glu Thr Glu Phe Asp Ser Leu Phe Pro
1               5                   10                  15

Glu Asp Asp Leu
            20

<210> SEQ ID NO 56
<211> LENGTH: 20
<212> TYPE: PRT
<213> ORGANISM: Homo Sapien
<220> FEATURE:
<221> NAME/KEY: VARIANT
<222> LOCATION: 1
<223> OTHER INFORMATION: Xaa is Val, Ile, or Leu
<220> FEATURE:
<221> NAME/KEY: VARIANT
<222> LOCATION: 2
<223> OTHER INFORMATION: Xaa is Arg or Lys
<220> FEATURE:
<221> NAME/KEY: VARIANT
<222> LOCATION: 4
<223> OTHER INFORMATION: Xaa is Glu or Asp
<220> FEATURE:
<221> NAME/KEY: VARIANT
<222> LOCATION: 8
<223> OTHER INFORMATION: Xaa is Glu or Asp
<220> FEATURE:

```
<221> NAME/KEY: VARIANT
<222> LOCATION: 9
<223> OTHER INFORMATION: Xaa is Thr or Val
<220> FEATURE:
<221> NAME/KEY: VARIANT
<222> LOCATION: 10
<223> OTHER INFORMATION: Xaa is Glu or Asp
<220> FEATURE:
<221> NAME/KEY: VARIANT
<222> LOCATION: 12
<223> OTHER INFORMATION: Xaa is Glu or Asp
<220> FEATURE:
<221> NAME/KEY: VARIANT
<222> LOCATION: 13
<223> OTHER INFORMATION: Xaa is Ser or Ala
<220> FEATURE:
<221> NAME/KEY: VARIANT
<222> LOCATION: 14
<223> OTHER INFORMATION: Xaa is Leu, Ile, or Val
<220> FEATURE:
<221> NAME/KEY: VARIANT
<222> LOCATION: 17
<223> OTHER INFORMATION: Xaa is Glu or Asp
<220> FEATURE:
<221> NAME/KEY: VARIANT
<222> LOCATION: 18
<223> OTHER INFORMATION: Xaa is Glu or Asp
<220> FEATURE:
<221> NAME/KEY: VARIANT
<222> LOCATION: 19
<223> OTHER INFORMATION: Xaa is Glu or Asp
<220> FEATURE:
<221> NAME/KEY: VARIANT
<222> LOCATION: 20
<223> OTHER INFORMATION: Xaa is Leu, Ile, or Val
<220> FEATURE:
<221> NAME/KEY: PHOSPHORYLATION
<222> LOCATION: 11, 15
<223> OTHER INFORMATION: Tyr is Tyr, phosphotyrosine, or sulfotyrosine

<400> SEQUENCE: 56

Xaa Xaa Pro Xaa His Pro Ala Xaa Xaa Tyr Xaa Xaa Xaa Tyr Pro
 1               5                  10                  15

Xaa Xaa Xaa Xaa
           20
```